US009808535B2

(12) United States Patent
Kuebelbeck et al.

(10) Patent No.: US 9,808,535 B2
(45) Date of Patent: *Nov. 7, 2017

(54) CONJUGATES FOR PROTECTION FROM NEPHROTOXIC ACTIVE SUBSTANCES

(71) Applicant: Merck Patent GmbH, Darmstadt (DE)

(72) Inventors: Armin Kuebelbeck, Bensheim (DE); Gregor Larbig, Gelnhausen (DE); Stefan Arnold, Muenster (DE); Walter Mier, Bensheim (DE); Uwe Haberkorn, Schwetzingen (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/889,553

(22) PCT Filed: Apr. 16, 2014

(86) PCT No.: PCT/EP2014/001025
§ 371 (c)(1),
(2) Date: Nov. 6, 2015

(87) PCT Pub. No.: WO2014/180533
PCT Pub. Date: Nov. 13, 2014

(65) Prior Publication Data
US 2016/0114054 A1 Apr. 28, 2016

(30) Foreign Application Priority Data

May 7, 2013 (EP) ..................................... 13002431

(51) Int. Cl.
A61K 47/48 (2006.01)
A61K 51/08 (2006.01)
(Continued)

(52) U.S. Cl.
CPC ...... A61K 47/48315 (2013.01); A61K 31/192 (2013.01); A61K 31/385 (2013.01); A61K 51/08 (2013.01)

(58) Field of Classification Search
CPC ................ A61K 31/192; A61K 31/385; A61K 47/48315
See application file for complete search history.

(56) References Cited

U.S. PATENT DOCUMENTS 8,466,104 B2 6/2013 Jonassen et al.
8,563,508 B2 10/2013 Jonassen et al.
(Continued)

FOREIGN PATENT DOCUMENTS

WO 2007/022774 A1 3/2007
WO 2011/009539 A1 1/2011

OTHER PUBLICATIONS

Franssen et al., Low Molecular Weight Proteins as Carrier for Renal Drug Targeting: Naproxen Coupled to Lysozyme via the Spacer L-Lactic Acid, Pharmaceutical Research, vol. 10(7):963-969 (1993).*

(Continued)

Primary Examiner — Randall L Beane
(74) Attorney, Agent, or Firm — Millen, White, Zelano & Branigan, P.C.

(57) ABSTRACT

The present invention relates to a conjugate containing at least one kidney-selective carrier molecule and at least one active compound which has a protective action for the kidney against nephrotoxic active compounds, to a process for the preparation of the conjugate, to the use thereof for the protection of the kidney against nephrotoxic active compounds, and to a medicament comprising the conjugate.

7 Claims, 6 Drawing Sheets

(51) Int. Cl.
A61K 31/192 (2006.01)
A61K 31/385 (2006.01)

(56) References Cited

U.S. PATENT DOCUMENTS

| | | | |
|---|---|---|---|
| 8,703,702 | B2 | 4/2014 | Jonassen et al. |
| 9,078,929 | B2 | 7/2015 | Kuebelbeck et al. |
| 2001/0029035 | A1* | 10/2001 | Eisenhut .......... A61K 47/48092 435/69.4 |
| 2009/0069242 | A1 | 3/2009 | Jonassen et al. |
| 2009/0208420 | A1* | 8/2009 | Briel ................. A61K 49/1869 424/9.323 |
| 2012/0122788 | A1 | 5/2012 | Kuebelbeck et al. |
| 2013/0217628 | A1 | 8/2013 | Jonassen et al. |
| 2013/0252891 | A1 | 9/2013 | Jonassen et al. |

OTHER PUBLICATIONS

Shiff et al., Experimental Cell Research, vol. 222:179-188 (1996).*
Dolman et al., Drug Targeting to the Kidney: Advances in the active targeting of therapeutics to proximal tubular cells, Advanced Drug Delivery Reviews, vol. 62:1344-1357 (2010).*
McGrath et al., Self-Assembling Nanostructures: Recognition and Ordered Assembly in Protein-Based Materials, Mat. Res. Soc. Symp. Proc., vol. 292:183-189, (1993).*
McGrath et al., Recognition and assembly using protein "building blocks", Macromolecular Symposia., vol. 77:183-189 (1994).*
Lyu et al., Energetic Contribution of Solvent-exposed Ion Pairs to Alpha-helix Structure, J. Mol. Biol., vol. 223:343-350 (1992).*
Kilarski et al., Antisera against three connexin43 fragments react with a 43-kD protein localized to gap junctions in myocardium and human myometrium, Folia Histochemica Et Cytobiologica (1994), vol. 32(4):219-224).*
International Search Report dated Dec. 10, 2014 issued in corresponding PCT/EP2014/001025 application (pp. 1-3).
H. Matsushima et al., "The Role of Oxygen Free Radicals in Cisplatin-Induced Acute Renal Failure in Rats", J Lab Clin. Med, vol. 131, No. 6 (Jun. 1998) pp. 518-526.
E.J.F. Franssen et al., "Low Molecular Weight Proteins as Carriers for Renal Drug Targeting. Preparation of Drug-Protein Conjugates and Drug-Spacer Derivatives and Their Catabolism in Renal Cortex Homogenates and Lysosomal Lysates", J. Med. Chem., vol. 35, No. 7 (1992) pp. 1246-1259.
Z. Zhang et al., "The Targeting of 14-Succinate Triptolide-Lysozyme Conjugate to Proximal Renal Tubular Epithelial Cells", Biomaterials, vol. 30 (2009) pp. 1372-1381.
L. Denby et al., "Development of Renal-Targeted Vectors Through Combined In Vivo Phage Display and Capsid Engineering of Adenoviral Fibers From Serotype 19p", Molecular Therapy, vol. 15, No. 9 (Sep. 2007) pp. 1647-1654.
S.R. Kumar et al., "In-Labeled Galectin-3-Targeting Peptide as a SPECT Agent for Imaging Breast Tumors", The Journal of Nuclear Medicine, vol. 49, No. 5 (May 2008) pp. 796-803.
G.T. Hermanson et al., "The Chemistry of Reactive Groups", Academic Press (1996) pp. 137-166.
R. Klinke et al., "Physiologie" (2009) pp. 359-366.
J.H. Sung et al., "Saturable Distribution of Tacrine Into the Striatal Extracellular Fluid of the Rat: Evidence of Involvement of Multiple Organic Cation Transporters in the Transport", Drug Metabolism and Disposition, vol. 33, No. 3 (2005) pp. 440-448.
C.H. Nijboer et al., "Targeting the p53 Pathway to Protect the Neonatal Ischemic Brain" Annals of Neurology, vol. 70, No. 2 (Aug. 2011) pp. 255-264.
Komarova et al., "Suppression of p53: A New Approach to Overcome Side Effects of Antitumor Therapy", Biochemistry, vol. 65, No. 1 (2000) pp. 41-48.
M. Kawamura et al., "Calpain Inhibitor MDL 28170 Protects Hypoxic-Ischemic Brain Injury in Neonatal Rats by Inhibition of Both Apoptosis and Necrosis", Brain Research, vol. 1037 (2005) pp. 59-69.
RR. Ruela-De-Sousa et al., "Cytotoxicity of Apigenin on Leukemia Cell Lines: Implications for Prevention and Therapy", Cell Death and Disease, vol. 1 (2010) pp. 1-12.
K. Belshline et al., "Sp1 Facilitates DNA Double-Strand Break Repair Through a Nontranscriptional Mechanism", Molecular and Cellular Biology, vol. 32, No. 18 (Sep. 2012) pp. 3790-3799.
E.M. Saleh et al., "Antagonism Between Curcumin and the Topoisomerase II Inhibitor Etoposide", Cancer Biology & Therapy, vol. 13, No. 11 (Sep. 2012) pp. 1058-1071.
C.N. Salinas et al., "The Enhancement of Chondrogenic Differentiation of Human Mesenchymal Stem Cells by Enzymatically Regulated RGD Functionalities", Biomaterials, vol. 29 (2008) pp. 2370-2377.
R. Haag et al., "Polymere Therapeutika: Konzepte and Anwendungen", Angew Chemie, vol. 118 (2006) pp. 1218-1237.
C.Q. Zhao et al., "Both Endoplasmic Reticulum and Mitochondria are Involved in Disc Cell Apoptosis and Intervertebral Disc Degeneration in Rats", Age, vol. 32 (2010) pp. 161-177.
G.B. Fields "Solid-Phase Peptide Synthesis", (1997)—M.I. Simon "Methods in Enzymology", (2002)—W.C. Chan "FMOC Solid Phase Peptide Synthesis: A Pratical Approach".
P. Tyle, "Iontophoretic Devices for Drug Delivery", Pharmaceutical Research, vol. 3, No. 6 (1986) pp. 318-326.
W. Mier et al., "Conjugation of DOTA Using Isolated Phenolic Active Esters: The Labeling and Biodistribution of Albumin as Blood Pool Marker", Bioconjugate Chem., vol. 16, No. 1 (2005) pp. 237-240.
N. Ihara et al., "Amplification of Inhibitory Activity of Catechin Against Disease-Related Enzymes by Conjugation on Poly(lysine)", Biomacromolecules, vol. 5, No. 5 (2004) pp. 1633-1636.
A.M. El-Mowafy et al., "Evaluation of Renal Protective Effects of the Green-Tea (EGCG) and Red Grape Resveratrol: Role of Oxidative Stress and Inflammatory Cytokines", Natural Product Research, vol. 25, No. 8 (Apr. 2011) pp. 850-856.
Q. Geng et al., "Peptide-Drug Conjugate Linked via a Disulfide Bond for Kidney Targeted Drug Delivery", Bioconjugate Chemistry, vol. 23 (Jun. 5, 2012) pp. 1200-1210.
M. Freissmuth et al., Pharmakologie & Toxikologie (Jan. 1, 2012)., pp. 1-15.
K. Luo et al., "Sumoylation of MDC1 is Important for Proper DNA Damage Response", The EMBO Journal, vol. 31, No. 13 (May 25, 2012) pp. 3008-3019.
K.C. Kim et al., "Baicalein (5,6,7-trihydroxyflavone) reduces Oxidative Stress-Induced DNA Damage by Upregulating the DNA Repair System", Cell Biol Toxicol, vol. 28 (Jul. 1, 2012) pp. 421-433.

* cited by examiner

SEQUENCE LISTING

```
<160> NUMBER OF SEQ ID NOS: 91

<210> SEQ ID NO 1
<211> LENGTH: 7
<212> TYPE: PRT
<213> ORGANISM: Artificial Sequence
<220> FEATURE:
<223> OTHER INFORMATION: Denby et al.: Molecular Therapy 15, 9, 2007,
      1647-1654

<400> SEQUENCE: 1

Ala Pro Ala Ser Leu Tyr Asn
1               5

<210> SEQ ID NO 2
<211> LENGTH: 7
<212> TYPE: PRT
<213> ORGANISM: artificial sequence
<220> FEATURE:
<223> OTHER INFORMATION: Denby et al.: Molecular Therapy 15, 9, 2007,
      1647-1654
```

```
<400> SEQUENCE: 2

His Ile Thr Ser Leu Leu Ser
1               5

<210> SEQ ID NO 3
<211> LENGTH: 16
<212> TYPE: PRT
<213> ORGANISM: artificial sequence
<220> FEATURE:
<223> OTHER INFORMATION: Kumar und Deutscher: The Journal of Nuclear
      Medicine 49, 5, 2008, 796-803; Geng et al.: Bioconjugate Chemistry
      23, 2012, 1200-1210

<400> SEQUENCE: 3

Ala Asn Thr Pro Cys Gly Pro Tyr Thr His Asp Cys Pro Val Lys Arg
1               5                   10                  15

<210> SEQ ID NO 4
<211> LENGTH: 4
<212> TYPE: PRT
<213> ORGANISM: artificial sequence
<220> FEATURE:
<223> OTHER INFORMATION: example for sequence according to formula (1);
      page 8, line 23 to page 9, line 15

<400> SEQUENCE: 4

Glu Lys Lys Lys
1

<210> SEQ ID NO 5
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 5

Glu Glu Lys Lys Lys Lys Lys
1               5

<210> SEQ ID NO 6
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 6

Glu Glu Lys Lys Lys Lys
1               5

<210> SEQ ID NO 7
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 7

Glu Glu Lys Lys Lys
1               5

<210> SEQ ID NO 8
<211> LENGTH: 4
```

```
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 8

Glu Glu Lys Lys
1

<210> SEQ ID NO 9
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 9

Glu Glu Glu Lys Lys Lys Lys Lys
1               5

<210> SEQ ID NO 10
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 10

Glu Glu Glu Lys Lys Lys Lys
1               5

<210> SEQ ID NO 11
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 11

Glu Glu Glu Lys Lys Lys
1               5

<210> SEQ ID NO 12
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 12

Glu Glu Glu Lys Lys
1               5

<210> SEQ ID NO 13
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 13

Glu Glu Glu Lys
```

```
<210> SEQ ID NO 14
<211> LENGTH: 9
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 14

Glu Glu Glu Glu Lys Lys Lys Lys
1               5

<210> SEQ ID NO 15
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 15

Glu Glu Glu Glu Lys Lys Lys Lys
1               5

<210> SEQ ID NO 16
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 16

Glu Glu Glu Glu Lys Lys Lys
1               5

<210> SEQ ID NO 17
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 17

Glu Glu Glu Glu Lys Lys
1               5

<210> SEQ ID NO 18
<211> LENGTH: 10
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 18

Glu Glu Glu Glu Glu Lys Lys Lys Lys Lys
1               5                   10

<210> SEQ ID NO 19
<211> LENGTH: 9
<212> TYPE: PRT
<213> ORGANISM: Artificial Sequence
<220> FEATURE:
<223> OTHER INFORMATION: example for sequence according to formula (1);
``` page 8, line 23 to page 9, line 15

<400> SEQUENCE: 19

Glu Glu Glu Glu Glu Lys Lys Lys Lys
1               5

<210> SEQ ID NO 20
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 20

Glu Glu Glu Glu Glu Lys Lys Lys
1               5

<210> SEQ ID NO 21
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 21

Glu Glu Glu Glu Glu Glu Lys Lys
1               5

<210> SEQ ID NO 22
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 22

Asp Lys Lys Lys
1

<210> SEQ ID NO 23
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 23

Asp Asp Lys Lys Lys Lys Lys
1               5

<210> SEQ ID NO 24
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 24

Asp Asp Lys Lys Lys Lys
1               5

<210> SEQ ID NO 25

```
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 25

Asp Asp Lys Lys Lys
1               5

<210> SEQ ID NO 26
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 26

Asp Asp Lys Lys
1

<210> SEQ ID NO 27
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 27

Asp Asp Asp Lys Lys Lys Lys Lys
1               5

<210> SEQ ID NO 28
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 28

Asp Asp Asp Lys Lys Lys Lys
1               5

<210> SEQ ID NO 29
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 29

Asp Asp Asp Lys Lys Lys
1               5

<210> SEQ ID NO 30
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 30
```

```
Asp Asp Asp Lys Lys
1               5

<210> SEQ ID NO 31
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 31

Asp Asp Asp Lys
1

<210> SEQ ID NO 32
<211> LENGTH: 9
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 32

Asp Asp Asp Asp Lys Lys Lys Lys Lys
1               5

<210> SEQ ID NO 33
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 33

Asp Asp Asp Asp Lys Lys Lys Lys
1               5

<210> SEQ ID NO 34
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 34

Asp Asp Asp Asp Lys Lys Lys
1               5

<210> SEQ ID NO 35
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 35

Asp Asp Asp Asp Lys Lys
1               5

<210> SEQ ID NO 36
<211> LENGTH: 10
<212> TYPE: PRT
<213> ORGANISM: Artificial Sequence
<220> FEATURE:
```

```
<223> OTHER INFORMATION: example for sequence according to formula (1);
      page 8, line 23 to page 9, line 15

<400> SEQUENCE: 36

Asp Asp Asp Asp Asp Lys Lys Lys Lys Lys
1               5                   10

<210> SEQ ID NO 37
<211> LENGTH: 9
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 37

Asp Asp Asp Asp Asp Lys Lys Lys Lys
1               5

<210> SEQ ID NO 38
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 38

Asp Asp Asp Asp Asp Lys Lys Lys
1               5

<210> SEQ ID NO 39
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 39

Asp Asp Asp Asp Asp Asp Lys Lys
1               5

<210> SEQ ID NO 40
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 40

Glu Arg Arg Arg
1

<210> SEQ ID NO 41
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 41

Glu Glu Arg Arg Arg Arg Arg
1               5
```

```
<210> SEQ ID NO 42
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 42

Glu Glu Arg Arg Arg Arg
1               5

<210> SEQ ID NO 43
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 43

Glu Glu Arg Arg Arg
1               5

<210> SEQ ID NO 44
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 44

Glu Glu Arg Arg
1

<210> SEQ ID NO 45
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 45

Glu Glu Glu Arg Arg Arg Arg Arg
1               5

<210> SEQ ID NO 46
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 46

Glu Glu Glu Arg Arg Arg Arg
1               5

<210> SEQ ID NO 47
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 47
```

Glu Glu Glu Arg Arg Arg
1               5

<210> SEQ ID NO 48
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 48

Glu Glu Glu Arg Arg
1               5

<210> SEQ ID NO 49
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 49

Glu Glu Glu Arg
1

<210> SEQ ID NO 50
<211> LENGTH: 9
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 50

Glu Glu Glu Glu Arg Arg Arg Arg Arg
1               5

<210> SEQ ID NO 51
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 51

Glu Glu Glu Glu Arg Arg Arg Arg
1               5

<210> SEQ ID NO 52
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 52

Glu Glu Glu Glu Arg Arg Arg
1               5

<210> SEQ ID NO 53
<211> LENGTH: 6
<212> TYPE: PRT
<213> ORGANISM: Artificial Sequence

```
<220> FEATURE:
<223> OTHER INFORMATION: example for sequence according to formula (1);
      page 8, line 23 to page 9, line 15

<400> SEQUENCE: 53

Glu Glu Glu Glu Arg Arg
1               5

<210> SEQ ID NO 54
<211> LENGTH: 10
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 54

Glu Glu Glu Glu Glu Arg Arg Arg Arg Arg
1               5                   10

<210> SEQ ID NO 55
<211> LENGTH: 9
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 55

Glu Glu Glu Glu Glu Arg Arg Arg Arg
1               5

<210> SEQ ID NO 56
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 56

Glu Glu Glu Glu Glu Arg Arg Arg
1               5

<210> SEQ ID NO 57
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 57

Glu Glu Glu Glu Glu Glu Arg Arg
1               5

<210> SEQ ID NO 58
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 58

Glu Lys Arg Lys
1
```

```
<210> SEQ ID NO 59
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 59

Glu Asp Lys Lys Arg Arg Lys
1               5

<210> SEQ ID NO 60
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 60

Glu Asp Lys Lys Lys Lys
1               5

<210> SEQ ID NO 61
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 61

Glu Cys Lys Lys His
1               5

<210> SEQ ID NO 62
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 62

Glu Asp Lys Lys
1

<210> SEQ ID NO 63
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 63

Asp Glu Glu Lys Lys Lys His Lys
1               5

<210> SEQ ID NO 64
<211> LENGTH: 7
<212> TYPE: PRT
<213> ORGANISM: Artificial Sequence
<220> FEATURE:
<223> OTHER INFORMATION: example for sequence according to formula (1);
      page 8, line 23 to page 9, line 15
```

```
<400> SEQUENCE: 64

Glu Asp Asp Lys Lys Lys
1               5

<210> SEQ ID NO 65
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 65

Glu Asp Glu Arg Arg Arg
1               5

<210> SEQ ID NO 66
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 66

Asp Cys Glu Lys His
1               5

<210> SEQ ID NO 67
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 67

Asp Glu Glu Lys
1

<210> SEQ ID NO 68
<211> LENGTH: 9
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 68

Asp Glu Asp Glu Arg Lys Arg Lys Arg
1               5

<210> SEQ ID NO 69
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 69

Asp Glu Glu Asp Lys Lys Lys His
1               5

<210> SEQ ID NO 70
<211> LENGTH: 7
<212> TYPE: PRT
```

```
<213> ORGANISM: Artificial Sequence
<220> FEATURE:
<223> OTHER INFORMATION: example for sequence according to formula (1);
      page 8, line 23 to page 9, line 15

<400> SEQUENCE: 70

Glu Asp Cys Glu Lys Arg His
1               5

<210> SEQ ID NO 71
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 71

Glu Asp Asp Glu Lys Lys
1               5

<210> SEQ ID NO 72
<211> LENGTH: 10
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 72

Glu Glu Glu Glu Glu Lys Lys Arg Arg Lys
1               5                   10

<210> SEQ ID NO 73
<211> LENGTH: 9
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 73

Glu Glu Glu Glu Asp Lys Lys Arg Lys
1               5

<210> SEQ ID NO 74
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 74

Glu Asp Asp Glu Glu Lys Lys Arg
1               5

<210> SEQ ID NO 75
<211> LENGTH: 8
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 75

Asp Asp Glu Glu Glu Glu Lys Lys
1               5
```

```
<210> SEQ ID NO 76
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 76

Lys Lys Glu Glu Glu
1               5

<210> SEQ ID NO 77
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 77

Arg Arg Glu Glu Glu
1               5

<210> SEQ ID NO 78
<211> LENGTH: 4
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 78

Lys Lys Glu Glu
1

<210> SEQ ID NO 79
<211> LENGTH: 6
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 79

Lys Lys Lys Glu Glu Glu
1               5

<210> SEQ ID NO 80
<211> LENGTH: 5
<212> TYPE: PRT
<213> ORGANISM: Artificial Sequence
<220> FEATURE:
<223> OTHER INFORMATION: example for sequence according to formula (1);
      page 8, line 23 to page 9, line 15

<400> SEQUENCE: 80

Lys Lys Lys Glu Glu
1               5

<210> SEQ ID NO 81
<211> LENGTH: 16
<212> TYPE: PRT
<213> ORGANISM: Artificial Sequence
<220> FEATURE:
<223> OTHER INFORMATION: examples for peptides according to the present
      invention; page 10, lines 21-22
```

```
<400> SEQUENCE: 81

Arg Arg Glu Glu Glu Arg Arg Glu Glu Glu Arg Arg Glu Glu Glu Arg
1               5                   10                  15

<210> SEQ ID NO 82
<211> LENGTH: 21
<212> TYPE: PRT
<213> ORGANISM: Artificial Sequence
<220> FEATURE:
<223> OTHER INFORMATION: examples for peptides according to the present
      invention; page 10, lines 21-22

<400> SEQUENCE: 82

Lys Lys Glu Glu Lys Lys Glu Glu Lys Lys Glu Glu Lys Lys Glu Glu
1               5                   10                  15

Lys Lys Glu Glu Lys
            20

<210> SEQ ID NO 83
<211> LENGTH: 16
<212> TYPE: PRT
<213> ORGANISM: Artificial Sequence
<220> FEATURE:
<223> OTHER INFORMATION: examples for peptides according to the present
      invention; page 10, lines 21-22

<400> SEQUENCE: 83

Lys Lys Lys Glu Glu Lys Lys Lys Glu Glu Lys Lys Lys Glu Glu Lys
1               5                   10                  15

<210> SEQ ID NO 84
<211> LENGTH: 19
<212> TYPE: PRT
<213> ORGANISM: Artificial Sequence
<220> FEATURE:
<223> OTHER INFORMATION: examples for peptides according to the present
      invention; page 10, lines 21-22

<400> SEQUENCE: 84

Lys Lys Lys Glu Glu Glu Lys Lys Lys Glu Glu Glu Lys Lys Lys Glu
1               5                   10                  15

Glu Glu Lys

<210> SEQ ID NO 85
<211> LENGTH: 16
<212> TYPE: PRT
<213> ORGANISM: Artificial Sequence
<220> FEATURE:
<223> OTHER INFORMATION: examples for peptides according to the present
      invention; page 10, lines 21-22

<400> SEQUENCE: 85

Lys Lys Glu Glu Glu Lys Lys Glu Glu Glu Lys Lys Glu Glu Glu Lys
1               5                   10                  15

<210> SEQ ID NO 86
<211> LENGTH: 4
<212> TYPE: PRT
<213> ORGANISM: Artificial Sequence
<220> FEATURE:
<223> OTHER INFORMATION: example for cleavable spacer; page 25, line 30

<400> SEQUENCE: 86

Asp Glu Val Asp
1
```

```
<210> SEQ ID NO 87
<211> LENGTH: 11
<212> TYPE: PRT
<213> ORGANISM: Artificial Sequence
<220> FEATURE:
<223> OTHER INFORMATION: Salinas et al. 2008, Biomaterials 29, 2370-2377

<400> SEQUENCE: 87

Cys Pro Glu Asn Phe Phe Trp Gly Gly Gly Gly
1               5                   10

<210> SEQ ID NO 88
<211> LENGTH: 5
<212> TYPE: PRT
<213> ORGANISM: Artificial Sequence
<220> FEATURE:
<223> OTHER INFORMATION: cleavable spacer, page 26, line 5

<400> SEQUENCE: 88

Pro Glu Asn Phe Phe
1               5

<210> SEQ ID NO 89
<211> LENGTH: 30
<212> TYPE: PRT
<213> ORGANISM: Artificial Sequence
<220> FEATURE:
<223> OTHER INFORMATION: Further examples for peptides according to the
      present invention; page 40, line 20 to page 41, line 10

<400> SEQUENCE: 89

Lys Lys Glu Glu Glu Lys Lys Glu Glu Glu Lys Lys Glu Glu Glu Lys
1               5                   10                  15

Lys Glu Glu Glu Lys Lys Glu Glu Glu Lys Lys Glu Glu Glu
            20                  25                  30

<210> SEQ ID NO 90
<211> LENGTH: 15
<212> TYPE: PRT
<213> ORGANISM: Artificial Sequence
<220> FEATURE:
<223> OTHER INFORMATION: Further examples for peptides according to the
      present invention; page 40, line 20 to page 41, line 10

<400> SEQUENCE: 90

Lys Lys Glu Glu Glu Lys Lys Glu Glu Glu Lys Lys Glu Glu Glu
1               5                   10                  15

<210> SEQ ID NO 91
<211> LENGTH: 18
<212> TYPE: PRT
<213> ORGANISM: Artificial Sequence
<220> FEATURE:
<223> OTHER INFORMATION: Further examples for peptides according to the
      present invention; page 40, line 20 to page 41, line 10

<400> SEQUENCE: 91

Lys Lys Lys Glu Glu Glu Lys Lys Glu Glu Glu Lys Lys Lys Glu Glu
1               5                   10                  15

Glu Lys
```

CONJUGATES FOR PROTECTION FROM NEPHROTOXIC ACTIVE SUBSTANCES

The present invention relates to a conjugate containing at least one kidney-selective carrier molecule and at least one active compound which has a protective action for the kidney against nephrotoxic active compounds, to a process for the preparation of the conjugate, to the use thereof for protection of the kidney against nephrotoxic active compounds, and to a medicament comprising the conjugate.

The kidney is of importance, in particular, for the transport and excretion of various substances and in the production of hormones. One function of the kidneys is the excretion of end products of metabolism, the so-called urophanic substances, and toxins from the body through the formation of urine, which is finally excreted from the body via the urinary tract. The kidney regulates the water balance and thus serves for long-term regulation of blood pressure. It regulates the electrolyte balance and the acid-base balance by control of the composition of urine. Furthermore, the kidney is an important organ for intermediary metabolism in the body (it effects gluconeogenesis). The kidney produces hormones, such as, for example, erythropoietin, for blood formation and is the site of degradation of peptide hormones. However, many functions of the kidney itself are also controlled by hormones.

Today, about 280 million people suffer from chronic kidney diseases. Many diagnostic and therapeutic methods have already been developed. For example, immunosuppressants, cytostatics, immunotherapeutic agents, antiphlogistics, antibiotics, virostatics, antihypertensives, uricosurics, or diuretics are employed for the treatment of the kidney or for influencing kidney function.

A number of approved active compounds, in particular cytostatics, exhibit nephrotoxicity as dose-limiting undesired side effect. Examples of substances having a nephrotoxic action are cisplatin, carboplatin, gentamicin or cyclophosphamide. For example, the widespread cytostatic cisplatin damages the proximal tubule cells (PTCs) of the kidneys, so that the dose in the case of single administration and the number of therapy cycles are restricted. Damage to the PTCs is caused by intracellular oxidative stress (Matsushima H, et al. 1998, Journal of Laboratory and Clinical Medicine, 131:518-526).

Amifostin is a cytoprotective medicament for which a chemo- and radioprotective action has been demonstrated in a large number of model organisms and in humans.

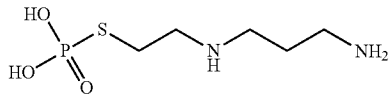 [SMILES: NCCCNCCSP(=O)(O)O]

Amifostin

Amifostin itself is a prodrug which is cleaved by alkaline phosphatases located in the membrane of the endothelial cells to give the actual active compound 2-((aminopropyl)amino)ethanethiol.

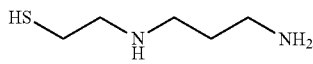

2-((Aminopropyl)amino)ethanethiol

Alkaline phosphatases are expressed to a significantly lesser extent in malignant tumour tissue than in healthy tissue. Consequently, amifostin is taken up principally by healthy cells. This selectivity—it is in the region of 100:1—is necessary in order to avoid also developing the chemo- and radioprotective action in the tumour cells. The active species is the antioxidative thiol group of 2-((aminopropyl)amino)ethanethiol.

Amifostin is not available in oral form. It is usually infused half an hour before radiotherapy or infusion of a chemotherapeutic agent. The dose here is in the range from 740 to 900 mg/m$^2$ of body surface area. In over half of patients, arterial hypotension is observed as a severe side effect.

There was therefore a need to protect the kidney better and more specifically against nephrotoxic active compounds during treatment (for example radiotherapy or infusion of a chemotherapeutic agent) in order to prevent the side effects of the active compounds.

The object of the present invention was therefore the provision of a solution for protecting the kidney specifically against nephrotoxic active compounds.

Surprisingly, it has been found that conjugates of kidney-selective carrier molecules and kidney-protecting active compounds are highly suitable for achieving this object.

The present invention therefore relates to a conjugate containing at least one kidney-selective carrier molecule and at least one active compound which has a protective action for the kidney against nephrotoxic active compounds.

In accordance with the invention, a kidney-selective carrier molecule is taken to mean a molecule which can serve as carrier (or transporter) for an active compound and enables targeted transport into the kidney. A carrier molecule which can be used in accordance with the invention is any compound which has sufficiently high kidney selectivity after conjugation with the active compound.

The prior art discloses, for example, the following substances which are suitable for targeting of the kidney, i.e. for targeted transport into the kidney:

Relatively small endogenous proteins, such as lysozyme (14.3 kDa), are able to pass through the glomerulus of the kidneys and are suitable as transporters for addressing of the kidneys with active compounds (Franssen et al.: *J. Med. Chem.* 35, 7, 1992, 1246-1259; Zhang et al.: *Biomaterials* 30, 2009, pp. 1372-1381).

Furthermore suitable in accordance with the invention are various peptides having about 5 to 20 amino acids which are taken up selectively by the kidneys. These are, for example, APASLYN (SEQ ID NO: 1) and HITSLLS (SEQ ID NO: 2) (Denby et al.: *Molecular Therapy* 15, 9, 2007, 1647-1654) or ANTPCGPYTHDCPVKR (SEQ ID NO: L (Kumar and Deutscher: *The Journal of Nuclear Medicine* 49, 5, 2008, 796-803; Geng et al.: *Bioconjugate Chemistry* 23, 2012, 1200-1210).

The kidney-selective carrier molecule is preferably a peptide which contains more than 50% (based on the number of amino acid units) of sequence sections of the formula (1)

$$-(A_n\text{-}B_m\text{-}C_o)-\quad\quad\quad(1),$$

where
A stands for an amino acid having an acidic side group,
B stands for an amino group having a basic side group,
C stands for any desired amino acid, n, m, independently of one another, stand for an integer from 1 to 10, where n:m=1:3 to 3:1,
o stands for an integer between 0 and 10,
and where
  the peptide overall has a chain length of 5 to 100 amino acid units
  and the peptide consists of at least 50% (based on the number of amino acid units) of amino acids A and B.

In accordance with the invention, a peptide is taken to mean a compound which has formed from linking of two or more amino acids via amide bonds. The individual amino acids here are connected in a defined sequence to form a chain.

In accordance with the invention, amino acids are compounds which carry at least one amino group and at least one carboxyl group. Examples are natural, proteinogenic amino acids or non-proteinogenic amino acids which occur in organisms or are prepared synthetically.

The amino acid units can be present in the D or L form in the peptide.

In accordance with the invention, the peptide comprises 5 to 100 amino acids. In a preferred embodiment, the peptide has a chain length of 5 to 40 amino acid units, particularly preferably a chain length of 10 to 30 amino acid units.

In accordance with the invention, the peptide consists of more than 50% (based on the number of amino acid units) of sequence sections of the formula (1)

$$-(A_n\text{-}B_m\text{---}C_o)- \qquad (1).$$

It preferably consists of more than 70% of sequence sections of the formula (1), particularly preferably more than 90%.

In formula (1), A stands for an amino acid having an acidic side group. This can be, for example, aspartic acid, glutamic acid, argininosuccinate and/or cysteic acid. Preference is given to amino acids having a carboxyl function, i.e. glutamic acid and/or aspartic acid, particularly preferably glutamic acid.

Within a peptide, A may stand for different amino acids having acidic side groups, i.e., for example, both glutamic acid and also aspartic acid, argininosuccinate and/or cysteic acid residues may be present simultaneously in the peptide.

In an alternative embodiment, the amino acids having acidic side groups A within a sequence section of the peptide are identical; in this case, for example, all amino acids A of the formula (1) in one sequence section of the peptide stand for aspartic acid, glutamic acid, argininosuccinate or cysteic acid, and those in a further sequence section of the peptide stand, independently of the above-mentioned sequence section, for aspartic acid, glutamic acid or cysteic acid.

In a further alternative embodiment, the amino acids having acidic side groups A within the peptide are identical; in this case, all amino acids A of the peptide stand, for example, for aspartic acid, glutamic acid, argininosuccinate or cysteic acid.

In a preferred embodiment, all amino acids A within the peptide stand for glutamic acid.

n in formula (1) defines the number of amino acid units A. n here stands for an integer from 1 to 10. n preferably stands for an integer from 1 to 5, particularly preferably for 2 or 3.

In formula (1), B stands for an amino acid having a basic side group. This can be, for example, lysine, arginine, histidine and/or ornithine. Preference is given to lysine.

Within a peptide, B may stand for different amino acids having basic side groups, i.e., for example, both lysine, arginine, histidine and/or ornithine residues may be present simultaneously in the peptide.

In an alternative embodiment, the amino acids having basic side groups B within a sequence section of the peptide are identical; in this case, for example, all amino acids B of the formula (1) in one sequence section of the peptide stand for lysine, arginine, histidine or ornithine, and those in a further sequence section of the peptide stand, independently of the above-mentioned sequence section, for lysine, arginine, histidine or ornithine. In a further alternative embodiment, the amino acids having basic side groups B within the peptide are identical; in this case, all amino acids B of the peptide stand, for example, for lysine, arginine, histidine or ornithine. In a preferred embodiment, all amino acids B within the peptide stand for lysine.

m in formula (1) defines the number of amino acid units B. m here stands for an integer from 1 to 10. m preferably stands for an integer from 1 to 5, particularly preferably for 2 or 3.

In formula (1), C stands for any desired amino acid. This can be, for example, alanine, arginine, asparagine, cysteine, glutamine, glycine, histidine, isoleucine, leucine, lysine, methionine, phenylalanine, proline, serine, threonine, tryptophan, tyrosine, valine and/or citrulline.

Preference is given to proteinogenic amino acids which are linked in a natural manner. This ensures degradation of the peptide in the proximal tubule cells of the kidneys to give toxicologically entirely benign metabolites. Within a peptide, C may stand for different amino acids.

o in formula (1) defines the number of amino acid units C. o here stands for an integer from 0 to 10. o preferably stands for 0, 1 or 2, particularly preferably for 0 or 1. In a very particularly preferred embodiment, o stands for 0, i.e. in this case no amino acid unit C is present in the peptide.

In a preferred embodiment, n and m stand, independently of one another, for 2 or 3.

In accordance with the invention, the ratio of n:m in formula (1) is 1:3 to 3:1. Illustrative embodiments of the sequence sections of the formula (1) are: $-(A_1\text{-}B_3\text{---}C_o)-$, $-(A_1\text{-}B_2\text{---}C_o)-$, $-(A_1\text{-}B_1\text{---}C_o)-$, $-(A_2\text{-}B_6\text{---}C_o)-$, $-(A_2\text{-}B_5\text{---}C_o)-$, $-(A_2\text{-}B_4\text{---}C_o)-$, $-(A_2\text{-}B_3\text{---}C_o)-$, $-(A_2\text{-}B_2\text{---}C_o)-$, $-(A_2\text{-}B_1\text{---}C_o)-$, $-(A_3\text{-}B_9\text{---}C_o)-$, $-(A_3\text{-}B_8\text{---}C_o)-$, $-(A_3\text{-}B_7\text{---}C_o)-$, $-(A_3\text{-}B_6\text{---}C_o)-$, $-(A_3\text{-}B_5\text{---}C_o)-$, $-(A_3\text{-}B_4\text{---}C_o)-$, $-(A_3\text{-}B_3\text{---}C_o)-$, $-(A_3\text{-}B_2\text{---}C_o)-$, $-(A_3\text{-}B_1\text{---}C_o)-$, $-(A_4\text{-}B_{10}\text{---}C_o)-$, $-(A_4\text{-}B_9\text{---}C_o)-$, $-(A_4\text{-}B_8\text{---}C_o)-$, $-(A_4\text{-}B_7\text{---}C_o)-$, $-(A_4\text{-}B_6\text{---}C_o)-$, $-(A_4\text{-}B_5\text{---}C_o)-$, $-(A_4\text{-}B_4\text{---}C_o)-$, $-(A_4\text{-}B_3\text{---}C_o)-$, $-(A_4\text{-}B_2\text{---}C_o)-$, $-(A_5\text{-}B_{10}\text{---}C_o)-$, $-(A_5\text{-}B_9\text{---}C_o)-$, $-(A_5\text{-}B_8\text{---}C_o)-$, $-(A_5\text{-}B_7\text{---}C_o)-$, $-(A_5\text{-}B_6\text{---}C_o)-$, $-(A_5\text{-}B_5\text{---}C_o)-$, $-(A_5\text{-}B_4\text{---}C_o)-$, $-(A_5\text{-}B_3\text{---}C_o)-$, $-(A_5\text{-}B_2\text{---}C_o)-$, $-(A_6\text{-}B_{10}\text{---}C_o)-$, $-(A_6\text{-}B_9\text{---}C_o)-$, $-(A_6\text{-}B_8\text{---}C_o)-$, $-(A_6\text{-}B_7\text{---}C_o)-$, $-(A_6\text{-}B_6\text{---}C_o)-$, $-(A_6\text{-}B_5\text{---}C_o)-$, $-(A_6\text{-}B_5\text{---}C_o)-$, $-(A_6\text{-}B_3\text{---}C_o)-$, $-(A_6\text{-}B_2\text{---}C_o)-$, $-(A_7\text{-}B_{10}\text{---}C_o)-$, $-(A_7\text{-}B_9\text{---}C_o)-$, $-(A_7\text{-}B_8\text{---}C_o)-$, $-(A_7\text{-}B_7\text{---}C_o)-$, $-(A_7\text{-}B_6\text{---}C_o)-$, $-(A_7\text{-}B_5\text{---}C_o)-$, $-(A_7\text{-}B_4\text{---}C_o)-$, $-(A_7\text{-}B_3\text{---}C_o)-$, $-(A_8\text{-}B_{10}\text{---}C_o)-$, $-(A_8\text{-}B_9\text{---}C_o)-$, $-(A_8\text{-}B_8\text{---}C_o)-$, $-(A_8\text{-}B_7\text{---}C_o)-$, $-(A_8\text{-}B_6\text{---}C_o)-$, $-(A_8\text{-}B_5\text{---}C_o)-$, $-(A_8\text{-}B_4\text{---}C_o)-$, $-(A_8\text{-}B_3\text{---}C_o)-$, $-(A_9\text{-}B_{10}\text{---}C_o)-$, $-(A_9\text{-}B_9\text{---}C_o)-$, $-(A_9\text{-}B_8\text{---}C_o)-$, $-(A_9\text{-}B_7\text{---}C_o)-$, $-(A_9\text{-}B_6\text{---}C_o)-$, $-(A_9\text{-}B_5\text{---}C_o)-$, $-(A_9\text{-}B_4\text{---}C_o)-$, $-(A_9\text{-}B_3\text{---}C_o)-$, $-(A_{10}\text{-}B_{10}\text{---}C_o)-$, $-(A_{10}\text{-}B_9\text{---}C_o)-$, $-(A_{10}\text{-}B_8\text{---}C_o)-$, $-(A_{10}\text{-}B_7\text{---}C_o)-$, $-(A_{10}\text{-}B_6\text{---}C_o)-$, $-(A_{10}\text{-}B_5\text{---}C_o)-$ or $-(A_{10}\text{-}B_4\text{---}C_o)-$, where A, B, C and o are defined as described above.

In accordance with the invention, the sequence of the formula (1) can stand, for example, for a sequence selected from:
-(EKKK)- (SEQ ID NO: 4), -(EKK)-, -(EK)-, -(EEKKKK)- (SEQ ID NO: 5), -(EEKKKK)- (SEQ ID NO: 6), -(EEKKK)- (SEQ ID NO: 7), -(EEKK)- (SEQ ID NO: 8), -(EEK)-, -(EEEKKKKK)- (SEQ ID NO: 9), -(EEEKKKK)- (SEQ ID NO: 10), -(EEEKKK)- (SEQ ID NO: 11), -(EEEKK)- (SEQ ID NO: 12), -(EEEK)- (SEQ ID NO: 13), -(EEEEKKKKK)- (SEQ ID NO: 14), -(EEEEKKKK)- (SEQ ID NO: 15), -(EEEEKKK)- (SEQ ID NO: 16), -(EEEEKK)- (SEQ ID NO: 17), -(EEEEEKKKKK)- (SEQ ID NO: 18), -(EEEEEKKKK)- (SEQ ID NO: 19), -(EEEEEKKK)- (SEQ ID NO: 20), -(EEEEEEKK)- (SEQ ID NO: 21), -(DKKK)- (SEQ ID NO: 22), -(DKK)-, -(DK)-, -(DDKKKKK)- (SEQ ID NO: 23), -(DDKKKK)- (SEQ ID NO: 24), -(DDKKK)- (SEQ ID NO: 25), -(DDKK)- (SEQ ID NO: 26), -(DDK)-, -(DDDKKKKK)- (SEQ ID NO: 27), -(DDDKKKK)- (SEQ ID NO: 28), -(DDDKKK)- (SEQ ID NO: 29), -(DDDKK)- (SEQ ID NO: 30), -(DDDK)- (SEQ ID NO: 31), -(DDDDKKKKK)- (SEQ ID NO: 32), -(DDDDKKKK)- (SEQ ID NO: 33), -(DDDDKKK)- (SEQ ID NO: 34), -(DDDDDKK)- (SEQ ID NO: 35), -(DDDDDKKKKK)- (SEQ ID NO: 36), -(DDDDDKKKK)- (SEQ ID NO: 37), -(DDDDDKKK)- (SEQ ID NO: 38), -(DDDDDDKK)- (SEQ ID NO: 39), -(ERRR)- (SEQ ID NO: 40), -(ERR)-, -(ER)-, -(EERRRRR)- (SEQ ID NO: 41), -(EERRRR)- (SEQ ID NO: 42), -(EERRR)- (SEQ ID NO: 43), -(EERR)- (SEQ ID NO: 44), -(EER)-, -(EEERRRRR)- (SEQ ID NO: 45), -(EEERRRR)- (SEQ ID NO: 46), -(EEERRR)- (SEQ ID NO: 47), -(EEERR)- (SEQ ID NO: 48), -(EEER)- (SEQ ID NO: 49), -(EEEERRRRR)- (SEQ ID NO: 50), -(EEEERRRR)- (SEQ ID NO: 51), -(EEEERRR)- (SEQ ID NO: 52), -(EEEERR)- (SEQ ID NO: 53), -(EEEEERRRRR)- (SEQ ID NO: 54), -(EEEEERRRR)- (SEQ ID NO: 55), -(EEEEERRR)- (SEQ ID NO: 56), -(EEEEEERR)- (SEQ ID NO: 57), -(EKRK)- (SEQ ID NO: 58), -(ERK)-, -(EDKKRRK)- (SEQ ID NO: 59), -(EDKKKK)- (SEQ ID NO: 60), -(ECKKH)- (SEQ ID NO: 61), -(EDKK)- (SEQ ID NO: 62), -(DEEKKKHK)- (SEQ ID NO: 63), -(EDDKKKK)- (SEQ ID NO: 64), -(EDERRR)- (SEQ ID NO: 65), -(DCEKH)- (SEQ ID NO: 66), -(DEEK)- (SEQ ID NO: 67), -(DEDERKRKR)- (SEQ ID NO: 68), -(DEEDKKKH)- (SEQ ID NO: 69), -(EDCEKRH)- (SEQ ID NO: 70), -(EDDEKK)- (SEQ ID NO: 71), -(EEEEEKKRRK)- (SEQ ID NO: 72), -(EEEEDKKRK)- (SEQ ID NO: 73), -(EDDEEKKR)- (SEQ ID NO: 74), -(DDEEEEKK)- (SEQ ID NO: 75), in each of which the one-letter codes of the amino acids are used: E (glutamic acid), D (aspartic acid), C (cysteine), K (lysine), R (arginine), H (histidine).

The sequence of the formula (1) preferably stands for a sequence selected from the group comprising -(KKEEE)- (SEQ ID NO: 76), -(RREEE)- (SEQ ID NO: 77), -(KKEE)- (SEQ ID NO: 78), -(KKKEEE) (SEQ ID NO: 79) and -(KKKEE)- (SEQ ID NO: 80).

The sequence of the formula (1) particularly preferably stands for the sequence -(KKEEE)- (SEQ ID NO: 76):

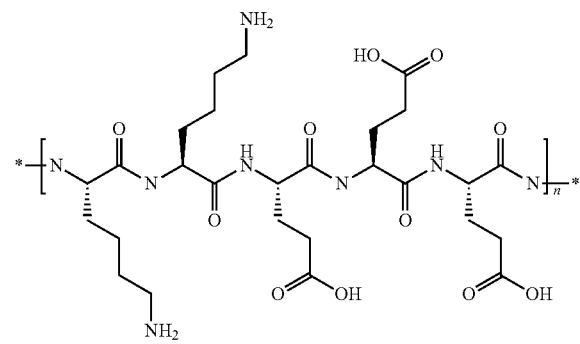

In accordance with the invention, the peptide consists of at least 50% (based on the number of amino acid units) of amino acids A and B. The peptide preferably consists of at least 70% (based on the number of amino acid units) of amino acids A and B, particularly preferably at least 80%.

In accordance with the invention, the sequence section of the formula (1) may be present in the peptide in total 1 to 50 times, preferably 1 to 30 times, particularly preferably 1 to 10 times, especially preferably 2 to 5 times.

In a possible embodiment, the peptide contains a plurality of directly successive sequence sections of the formula (1). The peptide preferably contains 3 to 5 successive sequence sections of the formula (1).

For example, the peptide may consist of 3 to 5 successive sequence sections of the formula (1) and one or more further amino acids at the C and/or N terminal. This is illustrated in formula (2):

$$X_p(A_nB_mC_o)_xY_q \qquad (2)$$

in which A, B, C, n, m and o are as defined above,
x stands for 3, 4, or 5,
X and Y stand, independently of one another, for any desired amino acid, preferably for A, and
p and q stand, independently of one another, for an integer between 0 and 3, preferably for 0 or 1.

Examples of possible peptides in the conjugate according to the invention are peptides selected from the group comprising $(RREEE)_3R$ (SEQ ID NO: 81), $(KKEE)_5K$ (SEQ ID NO: 82), $(KKKEE)_3K$ (SEQ ID NO: 83), $(KKKEEE)_3K$ (SEQ ID NO: 84) and $(KKEEE)_3K$ (SEQ ID NO: 85).

In an alternative embodiment of the present invention, the kidney-selective carrier molecule is an ε-polylysine conjugate, as described in WO 2011/009539 A1. This carrier molecule likewise enables highly selective concentration in the kidney. The lysine units in the polymer are linked via their ε-amino groups.

The present invention therefore furthermore also relates to a conjugate, as described above, characterised in that the at least one kidney-selective carrier molecule is a conjugate (2), containing at least one compound carrying carboxyl groups and an oligomer which consists of peptidically linked monomer units and which is either built up from more than 50% (based on the number of monomer units) of lysine monomer units, or contains at least 10 successive monomer units which are built up from at least 70% (based on the number of monomer units) of lysine monomer units, where the above-mentioned lysine monomer units in the oligomer are in each case linked via the ε-amino group of the side chain, characterised in that the proportion of carboxyl groups in the compound carrying carboxyl groups in the molecular weight of the compound carrying carboxyl groups is greater than 30%.

For the purposes of the present invention, the terms "ε-lysine monomer units" and "ε-lysine units" used below stand for lysine monomer units which are linked in the oligomer in each case via the ε-amino group of their side chain.

An ε-lysine unit has the following chemical structure:

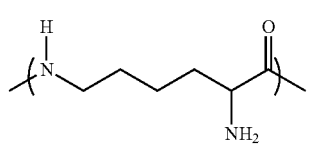

The ε-lysine monomer units can be in the D or L form in the oligomer.

In a preferred embodiment, the oligomer has a chain length of 10 to 50 monomer units.

In a preferred embodiment, at least one compound carrying carboxyl groups is bonded via the amino group of an ε-lysine monomer unit, i.e. one or more ε-lysine monomer units carry on their amino group a compound carrying carboxyl groups which is conjugated directly or via a spacer.

In an embodiment, the compound carrying carboxyl groups is a complexing agent, particularly preferably DOTA (=1,4,7,10-tetraazacyclododecane-N, -N', -N", -N'"-tetraacetic acid) or DTPA (diethylenetriaminepentaacetic acid).

A compound carrying carboxyl groups is a chemical compound which contains at least one carboxyl group (—COOH) and at least one group or functionality for bonding to the oligomer of conjugate (2). The bonding to the oligomer can take place in any known manner which results in covalent bonding of the oligomer and compound carrying carboxyl groups. Examples of functional groups via which bonding can take place are —NH$_2$, —SH, —OH, -Hal (for example —Cl, —Br, —I), -alkyne, —NCS, —NCO, —SO$_2$Cl, -azide, -carbonate, -aldehyde, -epoxide, —COOH, —COOR, where R in this case is preferably a halogen or preferably an activator, i.e. a good leaving group, such as, for example, N-hydroxysuccinimide, pentafluorophenyl or para-nitrophenyl. An overview of possible covalent types of coupling is found, for example, in "Bioconjugate Techniques", Greg T. Hermanson, Academic Press, 1996, on pages 137 to 165.

The compound carrying carboxyl groups preferably contains two or more carboxyl groups. These can be bonded directly or via a spacer to the carboxyl- and/or amino-terminal end of the oligomer and/or to functional group of the monomer units which is suitable for conjugation (for example NH, —NH$_2$, —COOH, —OH, —SH, -Hal (for example —Cl, —Br, —I), -alkyne, -azide, -aldehyde). Examples of compounds carrying carboxyl groups which are suitable in accordance with the invention are: citric acid, succinic acid, fumaric acid, maleic acid, glutamic acid, adipic acid, tartaric acid, oxalic acid, malonic acid, glutaric acid, adipic acid, suberic acid, azelaic acid, sebacic acid, the corresponding branched fatty acids, maleic acid, fumaric acid, cyclohexanedicarboxylic acid and the corresponding position isomers and similar aliphatic dibasic acids; tetrahydrophthalic acid, 5-norbornene-2,3-dicarboxylic acid and similar alicyclic dibasic acids; tricarballylic acid, aconitic acid, trimesic acid and similar tribasic acids; adamantanetetracarboxylic acid, butanetetracarboxylic acid, cyclopentanetetracarboxylic acid, tetrahydrofurantetracarboxylic acid and similar tetrabasic acids; sugar acids, in particular aldaric acids, such as, for example, glucaric acid, galactaric acid; malic acid, tartaric acid, citric acid and similar hydroxyfatty acids; trimellitic acid, pyromellitic acid, biphenyltetracarboxylic acid, benzophenonetetracarboxylic acid, diphenylsulfonetetracarboxylic acid and similar aromatic polycarboxylic acids.

In accordance with the invention, the compound carrying carboxyl groups can also be complexing agents which contain at least one carboxyl group, preferably two or more carboxyl groups, and at least one group or functionality for bonding to the oligomer of the conjugate according to the invention. Examples thereof are NOTA, TETA, EDTA or preferably DOTA or DTPA.

The compounds carrying carboxyl groups are typically bound via amino groups of the monomer units, for example the free amino group of ε-lysine.

Preferred compounds carrying carboxyl groups are those which contain two or more free carboxyl groups after conjugation to the oligomer.

It has been found that the specificity achieved in the targeting of the kidney is particularly high if the carboxyl groups of the compound carrying carboxyl groups make up a large proportion of the molar mass of the compound carrying carboxyl groups. Preference is therefore given to compounds carrying carboxyl groups in which the proportion of the carboxyl groups in the molar mass is greater than 30%, preferably greater than 40%.

Compounds carrying carboxyl groups which are particularly preferred in accordance with the invention are therefore those which contain two or more free carboxyl groups after conjugation to the oligomer and in which the proportion of the carboxyl groups in the molar mass is greater than 30%, preferably greater than 40%, such as, for example, DOTA, DTPA and citric acid.

It has been found that the conjugates accumulate particularly specifically in the kidney if a compound carrying carboxyl groups is covalently bonded to 10 to 80% of the monomer units.

The conjugate (2) should preferably contain at least one compound carrying carboxyl groups per 10 monomer units, particularly preferably between 3 and 6 compounds carrying carboxyl groups per 10 monomer units. Equally, however, it is also possible for one compound carrying carboxyl groups to be bonded to more than 9 of 10 monomer units or to all monomer units. The optimum number of compounds carrying carboxyl groups per 10 monomer units depends on the type of the compound carrying carboxyl groups and the type of the monomer units. The above-mentioned preferred number of compounds carrying carboxyl groups per monomer unit apply, in particular, to oligomers which are built up entirely from ε-lysine monomer units. The distribution of the compounds carrying carboxyl groups in conjugate (2) can be random, meaning that, for example, the first monomer units contain —NH$_2$, followed by a monomer unit with a compound carrying carboxyl groups, then again one containing —NH$_2$, then two times a monomer unit which carries a compound carrying carboxyl groups, then again twice one containing —NH$_2$, etc.

The term oligomer denotes the part of conjugate (2) that consists of an oligomer which consists of peptidically linked monomer units. The oligomer typically consists of 5 to 1000, preferably 8 to 100, particularly preferably 10 to 50, monomer units. In a particularly preferred embodiment, the oligomer consists of ε-polylysine which has between 8 and 100 monomer units, particularly preferably between 10 and 50 monomer units.

In other embodiments, however, up to 50% of the ε-lysine monomer units may be replaced by other monomer units and/or up to 50% of the ε-lysine monomer units may be derivatised or modified by the introduction of further functionalities. Likewise, the oligomer which consists of peptidically linked monomer units may contain a plurality of successive monomer units which are not ε-lysine monomer units if it contains at least 10 successive monomer units which consist of at least 70% (based on the number of monomer units), preferably at least 80%, of ε-lysine units. This is the case, for example, if a chain of 10 to 20 monomer units (for example comprising amino acids) in which no ε-lysine monomer unit is present and subsequently, for example, ten monomer units, of which eight are ε-lysine monomer units and two consist of other amino acids, is located at one end of the oligomer.

In accordance with the invention, the term monomer unit denotes any part of the oligomer that is peptidically linked to at least one further part of the oligomer. Terminal monomer units here are generally only peptidically linked to one further monomer unit. Monomer units in the middle of the oligomer are peptidically linked to two further monomer units. Monomer units which are peptidically linked to three further monomers are located at branching points. In the case of monomer units in the middle of the oligomer, the monomer unit typically provides on the one hand the —NH part of the peptidic bond and on the other hand the —CO part.

Typical other monomer units which the oligomer according to the invention can contain besides the ε-lysine monomer units are natural or synthetic amino acids, such as, in particular, alanine, β-alanine, glycine, glutamic acid, aspartic acid or arginine.

Further typical monomer units are monomer units having a spacer function of the formula

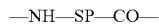   I where SP can be a C1 to C20 alkylene, alkenylene or alkynylene group, in which one or more non-adjacent methylene groups may be replaced by —O—, —S—, —S(O)—, —SO$_2$—, —SO$_2$O—, —C(O)—, —C(O)O—, —CH$_2$—, —CHR'—, —CR'$_2$—, —CR'═CH—, —CH—CR'—, —CH═CH—, —CR'═CR'—, —C≡C—, —N$^+$R'$_2$—, —P(O)R'O—, —C(O)NR'—, —SO$_2$NR'—, —OP(O)R'O—, —P(O)(NR'$_2$)NR'—, —PR'$_2$═N— or —P(O)R'— where R'═C$_1$- to C$_6$-alkyl, C$_3$- to C$_7$-cycloalkyl, unsubstituted or substituted phenyl.

SP preferably stands for linear C3 to C10-alkyl chains, linear C3-C10 chains having one or more alkylene groups, for ethylene glycol chains having two to ten ethylene glycol units or for oligopeptide chains.

Further typical monomer units are those which contain functionalities for the linking of spacers, active compounds, peptides, dyes, solubilisers, protecting groups, a solid phase or similar components or to which components such as active compounds, complexing agents, peptides, solubilisers, protecting groups, a solid phase or dyes are already bonded directly or via a spacer. Monomer units of this type preferably have at least one of the following functional groups —NH$_2$, —SH, —OH, -Hal (for example —Cl, —Br, —I), -alkyne, —NCS, —NCO, —SO$_2$Cl, -azide, -carbonate, -aldehyde, -epoxide, —COOH, —COOR, where R in this case is preferably a halogen or preferably an activator, i.e. a good leaving group, such as, for example, N-hydroxysuccinimide, pentafluorophenyl or para-nitrophenyl, or are linked to active compounds, complexing agents, peptides, dyes or similar components via a functional group of this type.

Furthermore, the oligomer according to the invention may contain ε-lysine monomer units which are derivatised. These are monomer units in which further functionalities (F1/F2) are correspondingly bonded to the NH group and/or the amino group.

In a preferred embodiment, the oligomer in conjugate (2) contains the amino acid cysteine. This embodiment has the advantage that the active compound can be bonded directly to the SH group of cysteine for protection of the kidneys. This bond can easily be broken intracellularly, enabling on the one hand the active compound to be released and on the other hand the SH group on the cysteine residue, which may itself have an antioxidative action, to become free again.

It is obvious to the person skilled in the art that the formulae depicted above depict monomer units in the middle of the oligomer chain and that terminal monomer units, depending on whether they are located at the C- or N-terminal end, in each case carry a COOH or COOR group instead of —CO— or carry an NH$_2$, NF1H, NF1R, NHR or NR$_2$ group instead of —NH— or —NF1-, where R is typically H, linear or branched C1-C6 alkyl, a spacer function for the bonding of active compounds, complexing agents, peptides, dyes, solubilisers, protecting groups, a solid phase or similar components, or an active compound, complexing agent, peptide, dye, solubiliser, protecting group, a solid phase or similar component bonded directly or via a spacer.

In accordance with the invention, an active compound which has a protective action for the kidney against nephrotoxic active compounds is taken to mean an active compound which reduces damage to the proximal tubule cells. For example, this is an active compound selected from antioxidants, apoptosis inhibitors, active compounds having an influence on the cell cycle, active compounds which activate the repair mechanisms of the cells, and combinations thereof.

In principle, damage to the proximal tubule cells can be reduced on several levels with the aid of these active compounds: In the first step, the uptake of cytotoxic compounds into the interior of the cells can be prevented by blockade of the transport mechanisms of the proximal tubule cells. The blockade can take place through specific inhibitors or alternatively also through sufficient amounts of the transport molecule itself, which temporarily blocks the receptors of the proximal tubule cells. A similar action is exhibited by substances which reduce the metabolic activity of the proximal tubule cells, or allow these cells to remain in the G$_0$ phase of the cell cycle.

In the second step, nephrotoxic compounds which have been transported or diffused into the cell can be rendered harmless by "antidotes" which have been channelled into the cell interior via the active compound transporter before administration of the nephrotoxic active compound.

The aim of the third step is to suppress apoptosis of damaged proximal tubule cells. Cytotoxic substances, such as, for example, cisplatin, cause damage to the DNA in the cell nucleus. If the damage level exceeds a certain threshold, programmed cell death, apoptosis, is triggered in the cell. In the case of tumour cells, this process is desired, but is fatal in the case of the proximal tumour cells of the kidneys. Some substances (apoptosis inhibitors) are known which are capable of preventing programmed cell death, or increasing the threshold for the initiation of apoptosis in the cell. In the fourth step, substances which activate the natural repair mechanisms of the cells and thus repair the DNA damage can be channelled into the cells.

Blockade of the Transport Mechanisms (Step 1):

Active compounds which have an influence on the transport mechanisms of the proximal tubule cells can be conjugated onto the kidney-selective carrier molecules. Cellular transporters both on the apical side of the proximal tubule cells, that is the side which is in the lumen and is in contact with the glomerular ultrafiltrate, and also on the basolateral side, that is the side which faces the blood vessels, can be blocked through specifically selected active compound molecules. Transporters of the basolateral side of the proximal tubule cells are of major importance for proximal tubule secretion of endogenous substances and foreign substances, such as, for example, medicaments. Anionic substances are taken up by the proximal tubule cells via organic anion transporter 1 (OAT1). Cationic substances, by contrast, via organic cation transporter 2 (OCT2). Both transporters can be inhibited by certain active compounds. An example of an inhibitor of OAT1 is the drug probenecid (Kurtz A, et al. 2009, Physiologie, ISBN 3-131-51496-5, p. 365). Probenecid can be conjugated onto a peptide according to the invention and, after glomerular filtration, taken up via the apical side of the proximal tubule cells. Through a labile linker, for example an ester group, by means of which the carboxyl group of probenecid is conjugated with the carrier molecule, the chemically unchanged active compound in the endosome of the proximal tubule cells can be liberated by esterases. The free active compound can reach the basolateral side through diffusion or transporters and block the organic anion transporter 1 there.

An example of an inhibitor of the organic cation transporter 2 is the drug tacrine (Sung J H, et al. 2005, Drug Metab Dispos, 33(3):440-448 PMID 15547049). Tacrine can also conjugate to a peptide according to the invention, for example as Schiff's base or amidically. The organic cation transporter 2 can thus be blocked by the route described in the example of conjugated probenecid. For example, the kidney-toxic cytostatic cisplatin is taken up and accumulated by the proximal tubule cells via OCT2 on the basolateral side. The cisplatin then develops its kidney-damaging action in the proximal tubule cells (Freissmuth M, et al. 2012, Pharmakologie & Toxikologie, ISBN 3-642-12353-8, p. 735).

Antioxidants (Step 2):

A number of substances with an antioxidative action can be conjugated onto the kidney-selective carrier molecules. Suitable classes of active compound are, inter alia, polyphenols (resveratrol, caffeic acid, luteolin, quercetin, rutin, cyanidin, xanthohumol, . . . ), lipoic acid, ascorbic acid, nicotinic acid, amifostin, alliin, thiols (for example 2-mercaptoethanesulfonate-sodium (mesna)), tocopherols, carotinoids and/or butylhydroxytoluene (BHT), or combinations thereof.

If the kidney-selective carrier molecule used is an ε-polylysine conjugate, as disclosed in WO 2011/009539 A1, the molecular structure of the oligomer can be varied by incorporating building blocks of the amino acid cysteine into the oligomer. Cysteine has a free thiol group having an antioxidative action. With this structure, the carrier can be modified to give an active medicament with an antioxidative action. Independently thereof, a number of protective active compounds can be conjugated onto the peptidic carrier instead or in addition, as described above.

Apoptosis Inhibitors (Step 3):

Anti-apoptotic substances can be conjugated onto the renal active compound transporter. Examples of this group of active compounds are pifithrin-µ (Nijboer et al. 2011, Ann Neurol.:doi: 10.1002/ana.22413) and pifithrin-α (Komarova et al. 2000, Biochemistry (Mosc) 65(1):41-48) as well as MDL 28170 (Kawamura et al. 2005, Brain Res. 1037(1-2): 59-69) and NS3694 (Zhao et al. 2010, Age (Dordr). 32(2): 161-177). Pifithrin-α, a p53 inhibitor, is able considerably to raise the threshold for the triggering of apoptosis in treated cells and model organisms.

An advantage of apoptosis inhibitors is that they can also be administered after damage to the cells. The disadvantage of systemic administration of apoptosis inhibitors, which may have the consequence of an increased risk of cancer, can advantageously be prevented by organ-specific administration—with the carrier molecule according to the invention.

Active Compounds Having an Influence on the Cell Cycle or Metabolism:

Besides the antioxidants and the apoptosis inhibitors, compounds which cause (temporary) stoppage of the cell cycle of the proximal tubule cells are likewise potential active compounds with which the damage to the kidneys by nephrotoxic medicaments can be reduced. An example thereof is the compound apigenin (Ruela-de-Sousa et al. 2010, Cell death & disease. 1, e19).

Active Compounds which Activate the Repair Mechanisms of the Cells (Step 4):

By activation of certain transcription factors, such as, for example, Sp1, or MDC1 (Luo et al. 2012, The EMBO journal, 31(13):3008-3019), a cell can be stimulated to increased repair of (double) strand breakages (Beishline et al. 2012, Molecular and cellular biology, DOI: 10.1128/MCB.00049-12. PMID 22826432). The flavonoid baicalein (5,6,7-trihydroxyflavone) is an example of a compound which is able to activate DNA repair in cells (Kim et al. 2012, Cell Biol Toxicol, DOI: 10.1007/s10565-012-9233-y. PMID 23011636).

In addition, cell cycle arrest (Step 1) puts the cell in a state in which essentially "repair work" is carried out on the damaged DNA (Saleh et al. 2012, Cancer biology & therapy 11, PMID 22895066).

The (simultaneous) administration of a number of classes of active compound (Steps 1 to 4 of the preceding examples) is particularly advantageous for keeping damage to the proximal tubule cells as low as possible. The individual active compounds here can either be conjugated onto separate transporter molecules or a plurality of different active compounds can be conjugated onto one transporter molecule.

Possible active compounds in the conjugate can therefore be selected from the group comprising antioxidants, apoptosis inhibitors, active compounds having an influence on the cell cycle, active compounds which activate the repair mechanisms of the cells, receptor inhibitors and combinations thereof.

In a preferred embodiment, the active compound which has a protective action for the kidney against nephrotoxic active compounds is an antioxidant and/or an apoptosis inhibitor.

Preferred antioxidants are lipoic acid, resveratrol, caffeic acid, luteolin, quercetin, rutin, cyanidin, xanthohumol, ascorbic acid, nicotinic acid, amifostin, alliin, thiols, mesna, tocopherols, carotinoids and butylhydroxytoluene (BHT).

Preferred apoptosis inhibitors are pifithrin-µ (Nijboer et al. 2011, Ann Neurol.:doi: 10.1002/ana.22413), pifithrin-α (Komarova et al. 2000, Biochemistry (Mosc) 65(1):41-48), MDL 28170 (Kawamura et al. 2005, Brain Res. 1037(1-2): 59-69) and NS3694 (Zhao et al. 2010, Age (Dordr). 32(2): 161-177).

In a particularly preferred embodiment of the present invention, the active compound which has a protective action for the kidney against nephrotoxic active compounds is therefore resveratrol, caffeic acid, luteolin, quercetin, rutin, cyanidin, xanthohumol, ascorbic acid, nicotinic acid, amifostin, alliin, thiols, tocopherols, carotinoids, butylhydroxytoluene (BHT), pifithrin-µ, pifithrin-α, MDL 28170 and/or NS3694, or mixtures thereof.

In accordance with the invention, the conjugate contains at least one kidney-selective carrier molecule, as defined above, and at least one active compound which has a protective action for the kidney against nephrotoxic active compounds, as defined above.

The bonding of the active compound to the carrier molecule is preferably covalent and can optionally take place via a spacer.

In accordance with the invention, one or more identical or different active compound molecules may be bonded per conjugate according to the invention.

Equally, the conjugate according to the invention, in particular in the case of macromolecules, such as relatively large active compound molecules, for example proteins, may also contain two or more carrier molecules which are bonded to one active compound molecule in order to facilitate kidney-specific concentration of the active compound. The carrier molecules are typically again covalently bonded to the macromolecule here. In accordance with the invention, macromolecules are taken to mean not only large molecules such as proteins, but instead also any form of particles (for example nanoparticles), liposomes or other systems by means of which active compounds can be transported or bonded to the active compounds.

Furthermore, functionalities for cell-specific targeting, such as, for example, antibodies, antibody fragments or aptamers, may be bonded to the conjugate according to the invention. Fluorescent dyes or interleukins, such as IL-2, may also be bonded.

The active compounds or other functionalities can be covalently bonded to the peptide directly or by means of a spacer.

A spacer, often also called linker, effects a covalent bond between two parts of a molecule, in the present case, for example, between the peptide and an active compound. A spacer is introduced, for example, if the connection between two moieties is not to take place only via a direct chemical bond, but instead a certain separation is to be generated between two moieties. Equally, a spacer can provide the chemical functionalities which are necessary in order to connect two parts of a molecule which would otherwise not react with one another. The conjugation of a spacer onto the carrier molecule or an active compound preferably takes place via an amide or ester bond. Spacers can be, for example, aliphatic hydrocarbons, polyethers (such as polyethylene glycols), peptides or similar elements having a chain structure. The spacer may be stable, i.e. it can only be cleaved to a slight extent or not at all under physiological conditions, or it may be unstable, i.e. it can be cleaved at least under certain physiological conditions.

Examples of functional groups via which direct bonding can take place are —$NH_2$, —SH, —OH, -Hal (e.g. —Cl, —Br, —I), -alkyne, —NCS, —NCO, $SO_2Cl$, -azide, -carbonate, -aldehyde, -epoxide, —COOH, —COOR, where R in this case is preferably a halogen or preferably an activator, i.e. a good leaving group, for example N-hydroxysuccinimide, pentafluorophenyl or para-nitrophenyl. An overview of possible covalent types of coupling can be found, for example, in "Bioconjugate Techniques", Greg T. Hermanson, Academic Press, 1996 on pages 137 to 165.

For example, active compounds may be bonded via a cleavable linker in the conjugate according to the invention. This linker is then cleaved in vivo under certain conditions, for example enzymatically or chemically, and releases the active compound. For this purpose, suitable linkers are those which contain carboxylate and disulfide bonds, in which the former groups are hydrolysed enzymatically or chemically and the latter are separated off by disulfide exchange, for example in the presence of glutathione.

An example of a cleavable spacer is also a peptide which can be cleaved specifically with the aid of specific, endogenous enzymes or alternatively those which are added to the body. Thus, for example, the peptide sequence DEVD (Asp-Glu-Val-Asp) (SEQ ID NO: MI is cleaved after apoptosis induction by caspase-3. For example, an active compound which is bonded via a spacer of this type can thus be removed from the kidney after a certain residence time therein, or alternatively a corresponding functionality (presence or absence of a certain enzyme) of the kidney can be checked. Further examples are the peptide sequences CPEN↓FFWGGGG (SEQ ID NO: 87) (Salinas et al. 2008, Biomaterials 29, 2370-2377) or PENFF (SEQ ID NO: 88), which can be cleaved by the matrix metalloprotease-13.

A simple embodiment of a cleavable spacer is the formation of a carboxylate, which can easily be cleaved by esterases.

In a preferred embodiment of the present invention, the active compound is therefore bonded via an ester link. This enables precise cleaving-off of the active compound molecule in the kidney. At the same time, however, the link is previously sufficiently stable for transport into the kidney in order to prevent premature cleaving-off.

Furthermore, a readily cleavable ester link of the active compound to the active compound transporter enables relatively fast release of the active compound at the target site. The cleavage of the ester link takes place more quickly in terms of time than the degradation of the active compound transporter by proteases.

Alternatively, the spacer may contain an acid-labile structure, for example a hydrazone, an imine, a carboxylhydrazone, an acetal or ketal (see, for example, Haag-R, Kratz-F, Angewandte Chemie page 1218 (2006)).

In accordance with the invention, the at least one active compound can be bonded to the N and/or C terminal of the carrier molecule.

In an alternative embodiment, the active compound can be bonded to an amino acid in the chain.

In a further alternative embodiment, the active compound can be bonded in the chain between the amino acids.

The conjugate according to the invention is taken up highly selectively by the kidneys and broken down relatively rapidly.

A suitable choice of the linking site of the active compound on the carrier molecule, and a suitable choice of the chain length and molecular structure of the carrier molecule, enables the desired pharmacokinetics, i.e. the desired active compound release at the target site, i.e. in the kidney, to be established here.

Typically, longer carrier molecules result in delayed release compared with shorter carrier molecules. Longer carrier molecules have, for example, chain lengths of 20 to 40 amino acids, preferably 30 amino acids, while shorter carrier molecules are typically taken to mean chain lengths of 3 to 10 amino acids, preferably 5 amino acids.

The release of active compounds linked at the C terminal takes place significantly more quickly than that of active compounds linked at the N terminal. Without being tied to this theory, it is assumed that the rate-determining step in peptide degradation is influenced, in particular, by carboxypeptidases, which break down the peptide starting from the C terminal.

In accordance with the invention, active compounds incorporated into the chain in a branched manner are also released significantly more slowly than those linked in a linear manner. The enzymatic degradation of branched peptide structures is basically significantly more difficult than the degradation of linear peptides.

Furthermore, the release rate of the active compound can, in accordance with the invention, also be controlled by the type of linking thereof to the oligomer. A readily cleavable ester link enables relatively fast release of the active compound at the target site (see above).

The present invention also relates to a process for the preparation of a conjugate, as described above, characterised in that an optionally activated active compound which has a protective action for the kidney against nephrotoxic substances is conjugated onto the carrier molecule.

The preparation of the conjugates according to the invention typically has at least the following process steps:
a) provision of a carrier molecule, as defined above, which contains at least one reactive group,
b) conjugation of at least one optionally activated active compound, as defined above, to the carrier molecule from step a).

The carrier molecules of the conjugates according to the invention can be prepared, in particular, by various processes known to the person skilled in the art in the area of peptide synthesis.

The preparation is typically carried out via a solid-phase synthesis.

In accordance with the invention, a solid phase is an organic, inorganic or organic/inorganic composite material which can be employed as resin or support in solid-phase synthesis. Furthermore, surfaces of mouldings, such as, for example, microtitre plates or particulate materials, such as, for example, organic or inorganic nanoparticles, metal particles or the like, are also regarded as solid phase in accordance with the invention.

The solid-phase synthesis is carried out in a corresponding manner to a conventional peptide synthesis (for example Fmoc/tBu peptide synthesis or Boc/benzyl peptide synthesis). Solid-phase syntheses of this type are known to the person skilled in the art. Suitable textbooks for peptide synthesis are "Solid-Phase Peptide Synthesis": 289 (Methods in Enzymology) by Sidney P. Colowick (author), Gregg B. Fields (publisher), Melvin I. Simon (publisher) Academic Press Inc (November 1997) or "Fmoc Solid Phase Peptide Synthesis: A Practical Approach" by W. Chan (author), W. C. Chan (publisher), Peter D. White (publisher) "Oxford Univ Pr (2 Mar. 2000). The monomers employed in each case are selected here in such a way that a peptide corresponding to the present invention is formed. Depending on the type of amino acid unit, the synthesis can be carried out using a derivatised amino acid unit directly or an amino acid unit which is firstly protected at the site intended for the derivatisation. When the synthesis of the peptide is complete, the final derivatisation with the active compound can then be carried out either in the solid phase or in solution after cleaving-off from the solid phase.

The bonding of the active compound in this case preferably takes place to the finished peptide, i.e. either still on the solid phase when the solid-phase synthesis of the peptide is complete or after the latter has been cleaved off in solution.

If the active compound is to be bonded, for example, to the N-terminal end of the peptide, the peptides are typically generated with an amino-terminal protecting group, such as, for example, Fmoc. If the active compound is able to withstand the conditions used on the one hand for cleaving off the peptide from the synthesis resin and on the other hand for deprotecting the side chains, the Fmoc group can be cleaved off from the N terminal of the complete resin-bonded peptide, enabling the active compound to be bonded to the free N-terminal amine. In such cases, the active compound is typically activated by processes which are generally known in the art for producing an active ester or active carbonate group which is effective for forming an amide or carbamate bond to the oligomer amino group. It is of course also possible to use a different linking chemistry.

In order to minimise side reactions here, guanidino and amidino groups may be blocked using conventional protecting groups, such as, for example, carbobenzyloxy groups (CBZ), di-t-BOC, PMC, Pbf, N—$NO_2$ and the like.

Coupling reactions are carried out by known coupling processes in solvents, such as, for example, N,N-dimethylformamide (DMF), N-methylpyrrolidone (NMP), dichloromethane (DCM) and/or water. Illustrative coupling reagents include O-benzotriazolyloxytetramethyluronium hexafluorophosphate (HATU), dicyclohexylcarbodiimide, bromo-tris(pyrrolidino)phosphonium bromide (PyBroP), etc. Other reagents may be present, such as, for example, N,N-dimethylaminopyridine (DMAP), 4-pyrrolidinopyridine, N-hydroxysuccinimide or N-hydroxybenzotriazole (HOBt).

A carrier molecule based on an $\epsilon$-polylysine conjugate, as described in WO 2011/009539 A1, can also be prepared starting from $\epsilon$-polylysine. Typically, synthetic or natural $\epsilon$-polylysine of uniform or different chain length is reacted here in solution with the corresponding compounds carrying carboxyl groups. To this end, for example, firstly the compounds carrying carboxyl groups can be activated. This can be carried out, for example, by activation of one or more of their carboxyl groups by converting them into the active ester or acid chloride. This is followed by the reaction with $\epsilon$-polylysine, with the conjugation preferably taking place onto the free amino groups. Alternatively, for example, one or more carboxyl groups of the compound carrying carboxyl groups can be activated by means of a coupling reagent, such as dicyclohexylcarbodiimide (DCC) or HATU, and reacted with the $\epsilon$-polylysine, with the conjugation preferably taking place onto the free amino groups. Reaction conditions for reactions of this type are known to the person skilled in the art. Suitable solvents are, for example, water, acetonitrile, DMSO, DMF, dioxane, THF, methanol or mixtures of two or more of the said solvents.

The conjugates according to the invention have the advantage that systemic side effects of active compounds for the treatment or imaging of the kidney can be substantially suppressed, since the conjugates enable targeted transport of kidney-protecting substances into the kidney. These kidney-damaging active compounds include, for example, cisplatin, carboplatin, gentamicin and cyclophosphamide. In the case of these substances, the nephrotoxicity limits the dose or the number of therapy cycles.

In connection with the treatment of the kidney with kidney-damaging substances, the administration of the conjugates according to the invention (for example by injection into the bloodstream or after subcutaneous injection) before, during or after the therapy enables targeted concentration of the protecting active compounds in the kidney.

The patient treated with a kidney-damaging substance, for example cisplatin, is given an injection of the kidney-protecting conjugate about 30 minutes before commencement of the therapy. The kidney-protecting conjugate can take place here by a single injection or by continuous infusion over the entire period of cisplatin administration, which usually extends over a period of one to two hours.

The present invention therefore also relates to a conjugate according to the invention, as described above, as medicament, such as, in particular, a therapeutic composition, in particular for protection of the kidney against nephrotoxic active compounds.

The present invention also relates to the use of a conjugate according to the invention, as described above, for protection of the kidney against nephrotoxic active compounds.

In this connection, the use of a carrier molecule of the formula (1), as defined above, is particularly advantageous, since this is extremely well suited to targeting of the kidney: compared with other known low-molecular-weight structures, it also exhibits very good concentration in the kidney in conjugation with the active compound. The comparison with peptides described in the literature which are taken up selectively by the kidneys (APASLYN (SEQ ID NO: 1) and HITSLLS (SEQ ID NO: 2), amino acids are indicated in single-letter code (Denby et al.: *Molecular Therapy* 15, 9, 2007, 1647-1654)) shows that, although most peptides have more or less highly pronounced kidney selectivity after intravenous administration, this is not the case in conjugation with an active compound. However, the pharmacological usefulness of the peptide structures as transport system for targeted protection of the kidney against nephrotoxic substances only arises if these peptides are taken up together with conjugated active compounds virtually exclusively by the kidneys, namely the proximal tubule cells. Only in this case does a significant advantage arise over systemic administration of the active compound.

Furthermore, the conjugates according to the invention enable subcutaneous and intraperitoneal administration of the peptide/active compound conjugates according to the invention to successfully address the kidneys besides the intravenous administration of peptides/proteins described in the literature for active compound transport into the kidneys.

The intraperitoneal, and specifically the subcutaneous administration route is advantageous for the administration of a potential active compound, compared with the intravenous route, for doctor and patient.

The present invention also relates to a medicament or a pharmaceutical composition, in particular a therapeutic or image-enhancing composition, comprising at least one conjugate according to the invention, as described above.

In accordance with the invention, the conjugate may also be in the form of its pharmaceutically usable salts and stereoisomers, including mixtures thereof in all ratios.

The use of the conjugates according to the invention for the preparation of a pharmaceutical composition or a medicament, in particular a therapeutic composition, is also in accordance with the invention.

In accordance with the invention, the present invention can also relate to a kit for the preparation of a medicament or a pharmaceutical composition, in particular a therapeutic composition, comprising at least one conjugate according to the invention. This conjugate can then be reacted, for example, with a suitable active compound, depending on the application, for the preparation of a therapeutic composition.

The present invention additionally relates to the conjugates according to the invention, and/or pharmaceutically usable salts and stereoisomers thereof, including mixtures thereof in all ratios, and optionally excipients and/or adjuvants
- as medicament
- for use as medicament
- as active compound or active component in a medicament
- for use for protection of the kidney against nephrotoxic active compounds
- and in particular as medicament for the treatment of diseases of the kidney.

A therapeutic composition, a pharmaceutical composition or a medicament generally consists at least of the active compound—in this case the conjugate according to the invention with bonded active compound—and one or more suitable solvents and/or excipients which allow application of the therapeutic composition.

Pharmaceutical compositions or medicaments can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or p-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity contains a prespecified amount of the compound. Syrups can be prepared by dissolving the compound in an aqueous solution with a suitable flavour, while elixirs are prepared using a non-toxic alcoholic vehicle. Suspensions can be formutated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The conjugates according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The conjugates according to the invention can also be delivered using monoclonal antibodies as individual carriers to which the conjugates are coupled. The conjugates can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-$\epsilon$-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

The conjugates according to the invention are preferably administered parenterally.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of the conjugate according to the invention depends on a number of factors, including the type of coupled active compound, the age and weight of the patient, the precise condition that requires treatment, and its severity, the nature of the formulation and the method of administration.

The present invention also relates to a kit for the preparation of a pharmaceutical composition, in particular an image-enhancing or therapeutic composition, at least comprising a conjugate according to the invention. The conjugate according to the invention can be in the kit in dissolved form in a solvent (for example an aqueous buffer) or preferably in the form of the lyophilisate.

It has been found that the conjugates according to the invention have already accumulated specifically, i.e. exclusively or virtually exclusively, in the kidney a short time after application. In the case of the preferred intravenous administration of the conjugates according to the invention, concentration in the kidney is observed after only 5 minutes. After one hour, more than 30%, preferably more than 50%, particularly preferably more than 70%, very particularly preferably more than 80%, of the injected dose is located in the kidney (% data based on measurement of the radioactivity).

In organ distribution studies with radiolabelled conjugates according to the invention (for example PET measurements or other non-invasive imaging), the conjugates according to the invention typically exhibit at least a two-fold, preferably at least a five-fold, particularly preferably at least a ten-fold concentration in the kidney in relation to the remainder of the body (blood, heart, lung, spleen, liver, muscle, brain) one hour after application. This means that the signal, which correlates directly with the amount of radiolabelled compound, in the kidney is at least twice as strong as the sum of the signals obtained from blood, heart, lung, spleen, liver, muscle and brain together.

In accordance with the invention, targeting of the kidney means the achievement of increased uptake of the applied substance in the kidney in relation to the remainder of the body. In the case of targeting of the kidney with the conjugate according to the invention, at least a two-fold, preferably at least a five-fold, particularly preferably at least a ten-fold concentration is preferably achieved in the kidney in relation to the remainder of the body (blood, heart, lung, spleen, liver, muscle, brain) by administration of a conjugate according to the invention. These values are determined by means of organ distribution studies with radiolabelled conjugates according to the invention (for example PET measurements or other non-invasive imaging).

The concentration in the kidney typically takes place after 30 minutes to 8 hours, depending on the type of application.

FIGURES

FIG. 1 shows the influence of the chain length on the release of active compound for the structures MAG3-KKEEEKKEEEKKEEEK (SEQ ID NO: 85) and MAG3-KKEEEKKEEEKKEEEKKEEEKKEEEKKEEE (SEQ ID NO: 89) (N-terminal linking of the active compound—FIG. 1, top) and KKEEEKKEEEKKEEE-y and KKEEEK-KEEEKKEEEKKEEEKKEEEKKEEE-y (C-terminal linking of the active compound—FIG. 1, bottom). Figure discloses "MAG3-(KKEEE)6" as SEQ ID NO: 89 and "MAG3-(KKEEE)3K" as SEQ ID NO: 85.

FIG. 2 shows the influence of the chain length on the release of active compound for the structure y-KKEEEK-KEEEKKEEEK (N-terminal linking of the active compound—FIG. 2, bottom) and the structures KKEEEK-KEEEKKEEE-y and KKEEEKKEEEKKEEEKKEEEKKEEEKKEEE-y (C-terminal linking of the active compound—FIG. 2, top).

FIG. 3 compares the organ distribution of the 125iodine-labelled conjugate y(KKEEE)$_3$K depending on the administration route.

Figure 1:
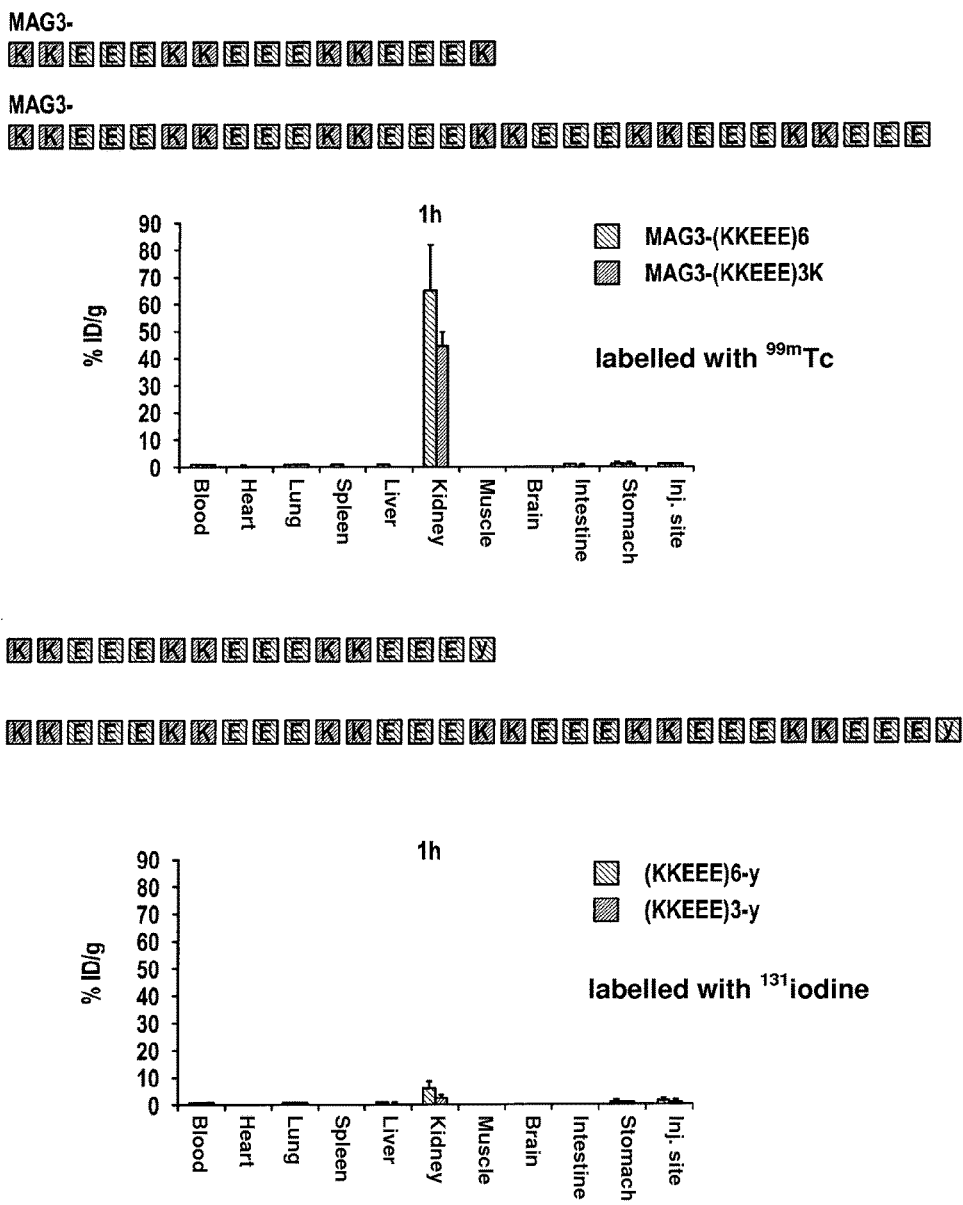

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

1. Material Syntheses

1.1. Synthesis of the Peptides Containing Acidic and Basic Side Groups

Solid-Phase Peptide Synthesis

The peptides are prepared on an ABI 433A fully automatic peptide synthesiser from Applied Biosystems GmbH (Carlsbad, Calif., USA) in accordance with the Fmoc/tBu strategy using Tentagel S RAM resin (degree of loading: 0.24 mmol/g; Rapp Polymere, Tübingen, Germany) as polymeric support.

Fmoc-amino acids (Fmoc-AA-OH; Novabiochem, Merck KGaA, Darmstadt, Germany) containing acid-labile side-chain protecting groups (for example Arg(Pbf), Asn(Trt), Asp(tBu), Cys(Trt), Gln(Trt), Glu(tBu), His(Trt), Lys(Boc), Ser(tBu), Thr(tBu), Tyr(tBu)) are used as starting materials. The synthesis cycle consists of a) cleaving-off of the Fmoc protecting group using 20% piperidine in NMP, b) washing steps with NMP, c) coupling: Fmoc-AA-OH/HBTU/DIPEA/peptide resin 10/10/20/1, 8 min, d) washing steps with NMP.

The effectiveness of the cleaving-off of Fmoc are monitored by means of automatic conductivity measurements. The peptides are cleaved off from the resin using TFA/H$_2$O/triisopropylsilane (95:2.5:2.5) (2 h at room temperature), precipitated out in cold methyl tert-butyl ether, separated by means of centrifugation (4000 rpm, 5 min), dried in vacuo and lyophilised from MeCN/H$_2$O (1:1).

Purification and Characterisation of Peptides

The purification of the peptide cleaved off from the resin is carried out by means of semipreparative HPLC using an LaPrep unit (VWR GmbH, Darmstadt, Germany). The column used is a Waters XBridge BEH130 PREP C18 (5 µm, 19×150 mm) column (flow rates: 9-20 ml/min; solvent: 0.1% of TFA in water to 0.1% of TFA in acetonitrile). The separation is carried out using a gradient from water to acetonitrile which is matched to the physico-chemical properties of the corresponding peptides. The purified peptide is obtained after lyophilisation.

For characterisation, the peptides prepared are analysed by means of analytical HPLC (Agilent 1100) and HPLC-MS (Exactive, Thermo Fisher Scientific). The HPLC analysis under standard conditions is carried out on the basis of a linear gradient from 0.1% of TFA in water to 0.1% of TFA in acetonitrile in 5 min (conditions: ChromolithR Performance RP-18e column, 100×3 mm; flow rate: 2 ml/min, wavelength=214 nm). For the mass spectrometry, an Agilent 1200 serves as HPLC system (conditions: Hypersil Gold C18 column, 0.21×200 mm, gradient: from 0.05% of TFA in water to 0.05% of TFA in acetonitirle in 30 min, flow rate: 200 µl/min, column oven: 60° C., wavelength=214 nm).

Radioactive Iodination of Peptides

The labelling is carried out using a 1 mM stock solution of the peptide to be labelled in water (DMSO may have to be added for better solubility). Tyrosine-containing peptides are labelled with iodine-123, iodine-125 or iodine-131 by means of the chloramine-T method (Perkin-Elmer, Waltham, Mass., USA). To this end, 20 µl of phosphate buffer (0.25 M, pH 7.4) are added to 10 µl of the stock solution, and the desired amount of radioactive iodine is added. For the labelling, 5 µl of chloramine-T (2 mg/ml of H$_2$O) are added.

The reaction is carried out for 30 seconds and is subsequently terminated using 10 µl of a saturated methionine solution. In order to separate off free iodine and by-products, the reaction mixture is purified by means of semipreparative HPLC (Chromolith RP-18e, 100×4.6 mm). The separation is carried out using a linear gradient from 0.1% of TFA in water to 0.1% of TFA in acetonitrile in 10 minutes (flow rate: 2 ml/min, UV absorption at 214 nm, γ detection). The solvent is subsequently removed in a rotary evaporator, and the labelled peptide is taken up in the desired buffer.

1.2. Synthesis of the ϵ-L-Polylysine Conjugates

ϵ-L-Polylysine-DOTA:

DOTA 2,6-Difluorophenyl Ester:

From DOTA and 2,6-difluorophenol with DCC (Mier et al. Bioconjugate Chem. 2005, 16, 237) ϵ-L-Polylysine, average molar mass about 4000 (principally consisting of 29-34 lysine units), is purchased as 25% aqueous solution from Chisso Corp. (Japan) and lyophilised. ϵ-Polylysine (30 mg) is dissolved in water (200 µl), and a solution of DOTA 2,6-difluorophenyl ester (100 mg) in methanol (1 ml) is added, and 100 µl of N,N-diisopropylethylamine are added, and the mixture is stirred at RT for 2 days. DOTA 2,6-difluorophenyl ester (100 mg) is then again added, and the mixture is stirred overnight at RT. The mixture is then diluted with water and purified preparatively by HPLC. Clean fractions are lyophilised together. DOTA-ϵ-polylysine (98 mg) is obtained as colourless solid substance. The number of DOTA units per molecule of ϵ-polylysine is determined by loading with Gd and by MS as being about 10 DOTA units per molecule of ϵ-polylysine; i.e. about 30% of the amino groups of the ϵ-polylysine have reacted.

ϵ-L-Polylysine-DTPA 75 mg of ϵ-L-polylysine and 310 mg of DTPA difluorophenyl ester tetra-t-butyl ester are dissolved in 4 ml of methanol and stirred at RT for 20 h. The reaction solution is evaporated, and 4 ml of TFA+100 µl of water are added to the residue and left to stand for 20 h. The product is precipitated using diethyl ether. Purification by HPLC and lyophilisation gives 150 mg as colourless solid.

1.3. Preparation of Lipoic Acid-y(KKEEE)₃K

The peptide y(KKEEE)₃K is prepared in a peptide synthesiser as described under 1.1 by means of solid-phase synthesis of the Fmoc/tBu strategy using the amino acids Fmoc-Lys(Boc)-OH, Fmoc-Glu(OtBu)-OH and Fmoc-Tyr(tBu)-OH (Novabiochem, Merck KGaA, Darmstadt, Germany). The peptide is initially not cleaved off from the resin, but instead suspended in NMP after the final Fmoc deprotection (1 ml of NMP are used per 100 mg of peptide resin). (RS)-lipoic acid (Merck KGaA, Darmstadt, Germany; in the meantime 4 equivalents based on the resin loading) is dissolved in NMP (1 ml per 100 mg), HBTU (4 eq.) is added, and the mixture is stirred at room temperature for about 10 min. The reaction mixture is added to the peptide resin, DIPEA (10 eq.) is added, and the mixture is shaken at room temperature for about 4 h. The resin is washed 5× with NMP and 5× with DCM and dried in vacuo for about 4 h. The lipoic acid/peptide conjugate is cleaved off from the resin using TFA/thioanisole/EDT/anisole (90/5/3/2) at room temperature for about 1 h, precipitated out in cold methyl tert-butyl ether, separated by means of centrifugation (4000 rpm, 5 min), dried in vacuo, lyophilised from MeCN/H₂O (1:1) and purified as described under 1.1 Purification and characterisation of the peptides.

Conjugates with other active compounds can also be prepared analogously.

1.4 Preparation of yKKK(Diacetylcaffeic Acid)(EEEKK)₂K(Diacetylcaffeic acid)EEEK For the peptic conjugation of diacetylcaffeic acid onto a lysine side chain, the amino acid Fmoc-Lys(Mmt)-OH is incorporated into the sequence of the peptide backbone. Before the cleaving-off, dichloromethane (DCM)/triisopropylsilane/TFA (94:5:1) is added to the peptide resin prepared under 1.1 for 3 min, and the mixture is washed 5× with DCM. This operation is repeated 3×. For coupling to the orthogonally deprotected side chain of lysine, 4 eq of diacetylcaffeic acid are dissolved in NMP, 4 eq of 1-ethyl-3-(3-dimethylaminopropyl)carbodiimide (EDC), 4 eq of ethyl cyano(hydroxyimino)acetate (Oxyma Pure) and 10 eq of diisopropylethylamine (DIPEA) are added, the mixture is stirred at room temperature for about 10 min and subsequently added to the peptide resin. The reaction mixture is shaken at room temperature for about 1 h, washed 5× with NMP and 5× with DCM and dried in vacuo. The functionalised peptide is cleaved off from the resin and purified as described under 1.1.

Conjugates with other active compounds can also be prepared analogously.

1.5 Preparation of y(KKKϵ(Lipoic Acid)EEE)₃K

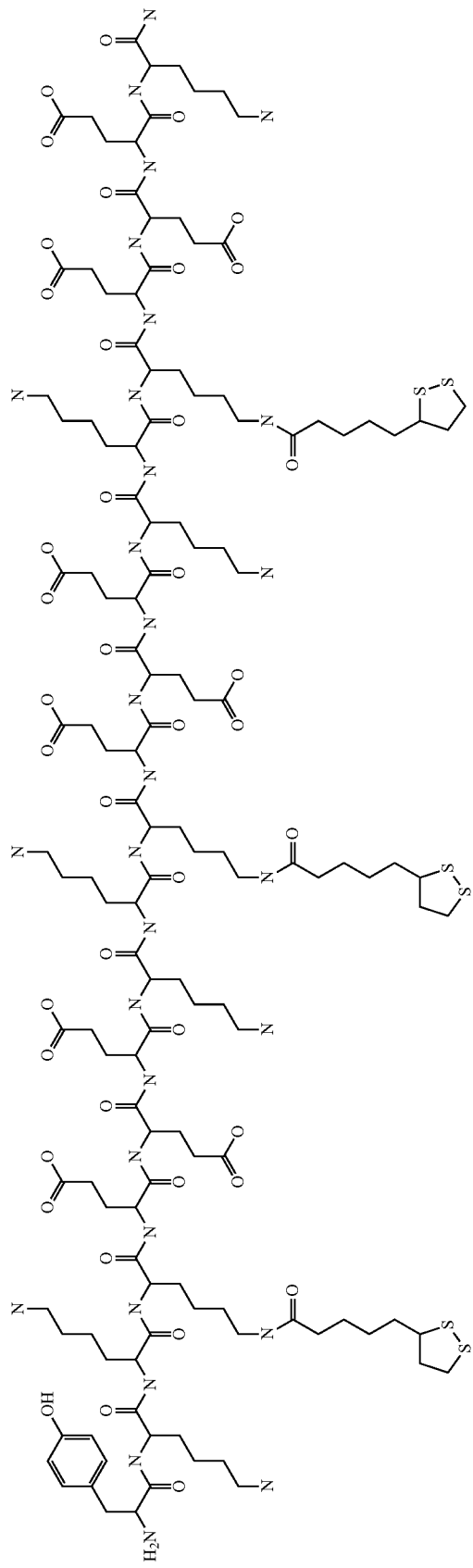
Molecular Weight = 3188.95
Exact Mass = 3185
Molecular Formula = C138H231N31O42S6
Molecular Composition = C 51.98% H 7.30% N 13.62% O 21.07% S 6.03%

1.5.1 Synthesis of the Fmoc-Lysine(ε-Lipoic Acid)-OH Building Block

N-Hydroxysuccinimide (1.15 g, 10 mmol), α-lipoic acid (2.02 g, 9.8 mmol) and (1.92 g, 10 mmol) of 1-ethyl-3-(3-dimethylaminopropyl)carbodiimide (EDAC) are dissolved in 50 ml of DMF and stirred at room temperature for about 4 h. 60 ml of ethyl acetate are then added to the batch. The organic phase is washed three times with 60 ml of distilled water, three times with 60 ml of saturated sodium hydrogencarbonate solution and once with saturated sodium chloride solution. The ethyl acetate phase is dried over $Na_2SO_4$, filtered and evaporated to dryness.

Yield: 2.23 g (73.5%)

Fmoc-Lys-OH (2.65 g, 7.2 mmol) is suspended in 110 ml of HEPES buffer (pH=7.4), and (2.14 g, 7.05 mmol) of lipoic acid active ester (dissolved in 130 ml of acetone) are added, and the mixture is stirred at room temperature. After a reaction time of about 3 h, the solution is adjusted to pH 7 by means of 0.1 N NaOH solution and stirred at room temperature for about 20 h. The batch is then brought to pH 9 using 0.1 N NaOH and washed twice with about 30 ml of ethyl acetate, subsequently adjusted to pH 3 using 1 N HCl and extracted three times with about 40 ml of ethyl acetate. The combined org. phases are washed with saturated sodium chloride solution, dried over Na2SO4, filtered and evaporated to dryness. Weight of crude product: 4.14 g (103. 25%)

The purification of the crude product is carried out by flash chromatography (stationary phase: silica gel 60, particle size: 15-40 μm, pre-packed by Götec-Labortechnik GmbH, mobile phase: chloroform, methanol (comprising 0.1% of HOAc), flow rate: 60 ml/min, loading: about 2 g, gradient: from 100% to 75% of chloroform in 18 min). The product fractions (Rt=9.1 min) are combined and evaporated to dryness.

Product weight: 3.18 g (77%)

1.5.2 Solid-Phase Peptide Synthesis

Peptides are prepared using a synthesiser from Applied Biosystems GmbH (Carlsbad, Calif., USA), model 433A, using the Fmoc/tBu strategy. The reactive side chains of the amino acids are protected as follows: Lys(Boc), Glu(tBu) and Tyr(tBu). Rink amide resin from Rapp-Polymere GmbH (degree of loading: 0.24 mmol/g) serves as solid phase. The corresponding amino acids, the Fmoc-lysine(ε-lipoic acid)-OH building block and HBTU are employed in 4-fold excess. The solvent used is NMP, and piperidine (20% in NMP) is used for the respective Fmoc cleaving off.

The protected peptide is cleaved off from the resin using TFA:thioanisole:anisole=90:8:2 (1 ml per 100 mg) (1-2 h), precipitated out in MTBE, centrifuged and dried.

1.5.3 Radioactive Iodination of Peptides

The tyrosine-containing peptides are labelled with $^{125}$iodine by means of the chloramine-T method. For the labelling, a 1 mM stock solution in water is used. If necessary, DMSO is added for better solubility. To this end, 20 μl of phosphate buffer (0.25 M, pH 7.4) are added to 10 μl of the stock solution, and the desired amount of radioactive iodine is added. The labelling is carried out using 5 μl of chloramine-T (2 mg/ml of $H_2O$). The reaction is carried out for 30 seconds and is subsequently terminated using 10 μl of a saturated methionine solution.

After the labelling, the peptide is purified by means of semi-preparative HPLC in order to remove the excess free iodine and other by-products. 100 μl of the 0.1 mM stock solution are in each case used for the injection. Before the injection, the radioactivity is recorded by means of a Geiger counter.

Conjugates with other active compounds can also be prepared analogously.

2. Use Examples

2.1. Organ Distribution Studies

In order to determine the pharmacokinetics, the radioactively labelled molecules from Example 1.1 to be investigated are injected into female NMRI mice via the tail vein (about 100 μl per animal). The animals (n=3 per time point) are subsequently sacrificed at the corresponding time points, dissected, and the distribution of the radioactivity in the isolated organs (liver, kidney, lung, spleen, intestine, brain, heart, blood, . . . ) is quantified by γ counter (Berthold LB951 G). The radioactivity measured per gram of organ/tissue based on the injected dose (ID) is determined and quoted as % of ID/g.

The influence of the chain length on the release of active compound is investigated. The structures MAG3-KKEEEK-KEEEKKEEEK (SEQ ID NO: 85), MAG3-KKEEEK-KEEEKKEEEKKEEEKKEEEKKEEE (SEQ ID NO: 89) and y-KKEEEKKEEEKKEEEK (N-terminal linking of the active compound—FIG. 1, top and FIG. 2 bottom) and the structures KKEEEKKEEEKKEEE-y and KKEEEK-KEEEKKEEEKKEEEKKEEE-y (C-terminal linking of the active compound—FIG. 1, bottom and FIG. 2, top) are investigated y here stands for iodotyrosine labelled with $^{125}$iodine; MAG3 stands for a mercaptoacetyltriglycine peptide fragment which complexes $^{99m}$Tc.

Figure 2:
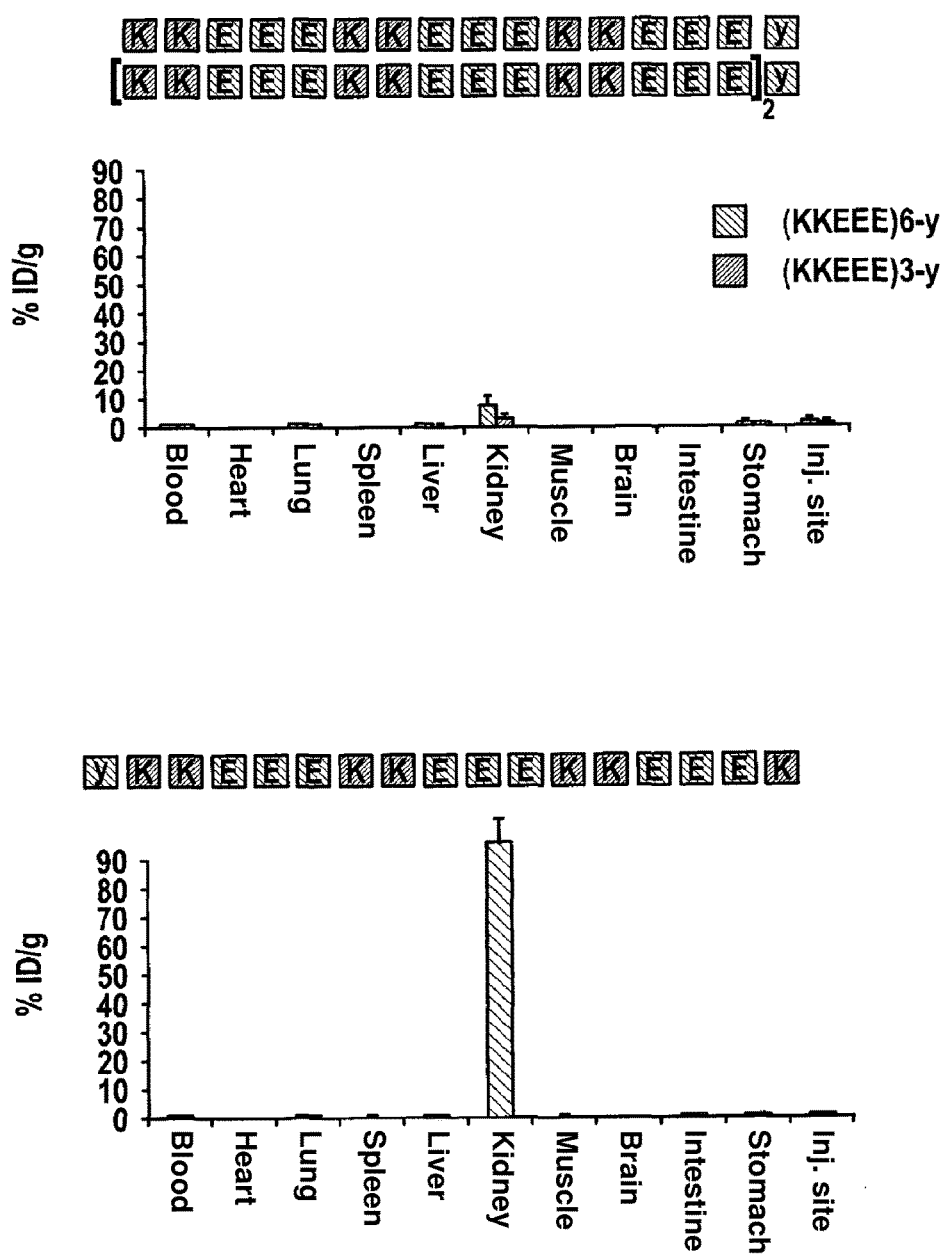

The result is depicted in FIGS. 1 and 2 (ID/g here stands for "injected dose per gram of tissue"): the release of radiolabelled tyrosine (as "active compound") is strongly influenced on the one hand via the chain length and on the other hand via the linking site of the "active compound" (C or N terminal). Basically, longer peptides result in delayed release. In addition, the release of tracers linked at the C terminal (iodotyrosine or also MAG3 with $^{99m}$Tc) proceeds significantly more quickly than in the case of N-terminal linking. The rate-determining step in the peptide degradation is apparently influenced, in particular, by carboxypeptidases, which break down the peptide starting from the C terminal.

The release kinetics of an active compound can be intentionally adjusted through the molecular structure of the peptide and the linking site of the active compound (C or N terminal).

2.2. Administration Route

Figure 3:
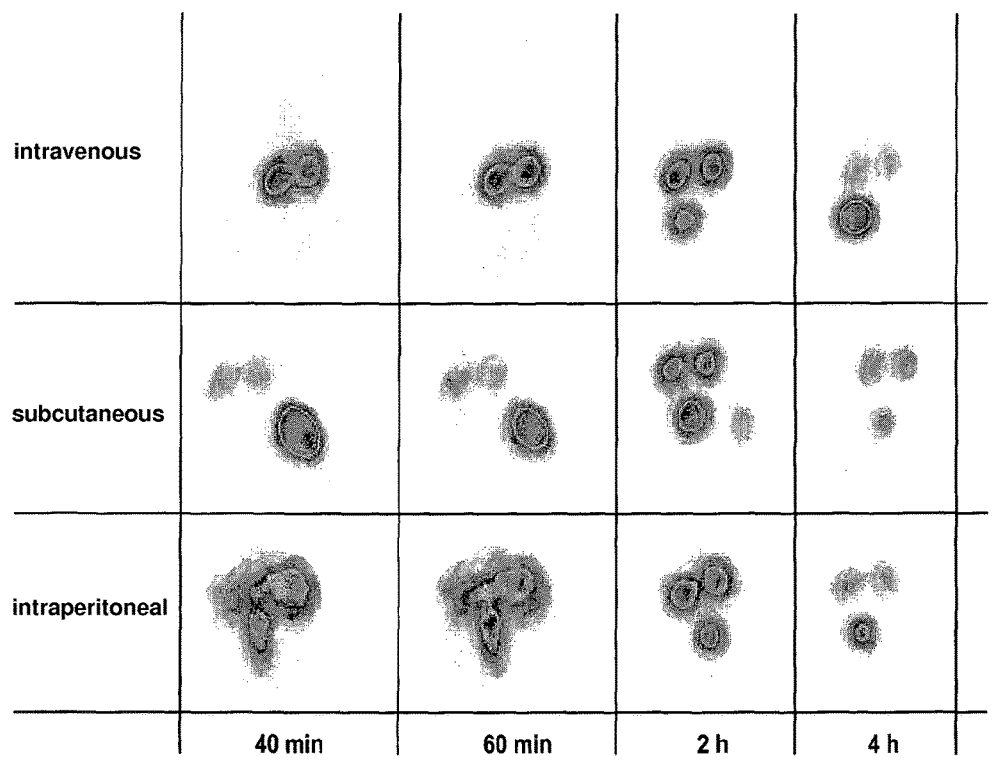

In further experiments, the administration route is investigated. To this end, nine NMRI mice are divided into three groups. All animals receive 10 mg/kg of body weight of a conjugate of D-tyrosine bonded to $(KKEEE)_3K$ (SEQ ID NO: 85) at the N terminal. Part of the conjugate is labelled with 131iodine on the D-tyrosine by means of the chloramine-T method. The labelled conjugate is administered intravenously to group 1, subcutaneously to group 2 and intraperitoneally to group 3. The conjugate here is dissolved in 100 μl of PBS buffer. SPECT scans of animals from the respective group are then carried out at various times (40, 60, 120 and 240 minutes). The results of this experimental series are depicted in FIG. 3. Besides the intravenous administration of peptides/proteins described in the literature for transport of active compound into the kidneys, subcutaneous and intraperitoneal administration of the peptides or peptide/active compound conjugates according to the invention can also successfully address the kidneys.

2.3. Scintigraphic Distribution of Diacetylcaffeic Acid Conjugates

In further experiments, the potential active compound diacetylcaffeic acid (DCA) is bonded both at the N terminal and also multiply to lysine side chains of the peptide backbone. The preparation of the N-terminal conjugate with y(KKEEE)$_3$K is carried out analogously as described under 1.3; the preparation of the diconjugated molecule (structure: yKKK(DCA)-EEEKKEEEKKK(DCA)EEEK) is carried out analogously as described under 1.4. The peptide/active compound conjugates obtained in this way are investigated for their kidney selectivity after labelling by means of iodine-125 and intravenous administration in the animal model mouse.

Figure 4:
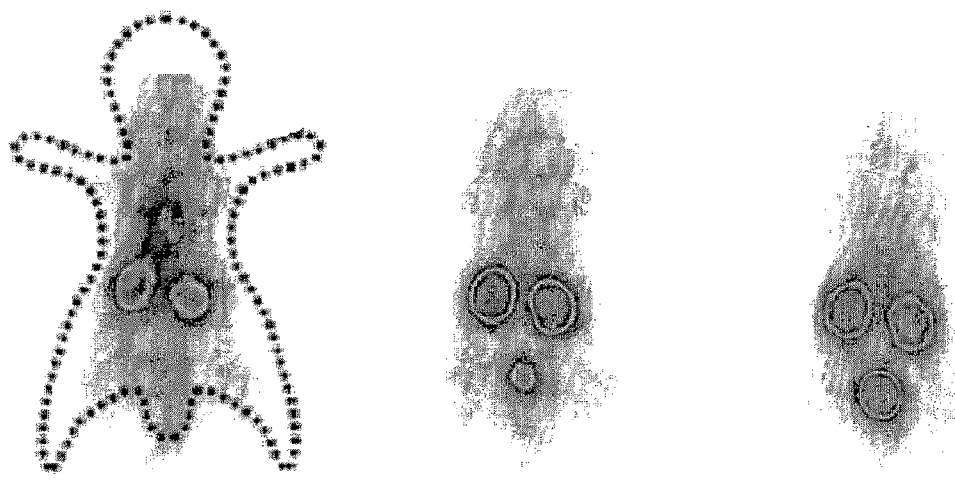
FIG. 4 shows the scintigraphic distribution of the diacetylcaffeic acid (KKEEE)$_3$K (SEQ ID NO: 85) active compound conjugate bonded at the N terminal after intravenous administration in an NMRI mouse.
Figure 5:
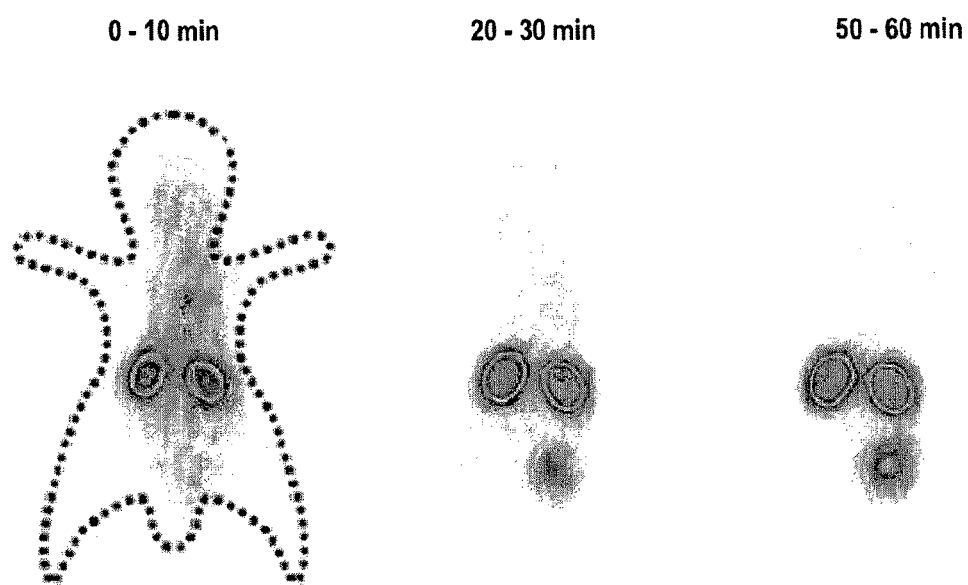
FIG. 5 shows the scintigraphic distribution of the diconjugated molecule yKKK(DCA)EEEKKEEEKKK(DCA) EEEK (CDA=diacetylcaffeic acid) after intravenous administration in an NMRI mouse.

Result (see FIGS. 4 and 5): the peptide/active compound conjugates prepared retain their high kidney specificity both after N-terminal bonding of diacetylcaffeic acid (FIG. 4) and also in the case of double bonding of diacetylcaffeic acid to different side chains of lysine of the peptide backbone (FIG. 5).

2.4. Protection of the Kidney

In a preclinical study, BALB/c mice are treated with doxorubicin. Each experimental animal receives a dose of 11 mg/kg of body weight. A control group is merely administered an isotonic saline solution. The animals treated with doxorubicin are divided into various groups. Group B receives an injection of free lipoic acid in the form of its potassium salt in addition to the doxorubicin injected. In the case of group C, the lipoic acid/peptide conjugate LA-(KKEEE)$_3$ (SEQ ID NO: 90) (lipoic acid on (Lys-Lys-Glu-Glu-Glu)$_3$ (SEQ ID NO: 90) N terminal) is administered by injection instead of free lipoic acid.

|  | Control | Doxorubicin | Doxorubicin + lipoic acid conjugate | Doxorubicin + lipoic acid |
| --- | --- | --- | --- | --- |
| Number of animals | 6 | 6 | 6 per dose; in the case of 3 doses = 18 animals | 6 per dose; in the case of 3 doses = 18 animals |
| Treatment | 0.9% salt solution | Doxorubicin hydrochloride diluted to 11 mg/kg of body weight in 0.9% salt solution | Doxorubicin hydrochloride diluted to 11 mg/kg of body weight in 0.9% salt solution | Doxorubicin hydrochloride diluted to 11 mg/kg of body weight in 0.9% salt solution |

2.5 Scintigraphic Distribution of Lipoic Acid Conjugates in Accordance with Example 1.5

In further experiments, the potential active compound lipoic acid is bonded via the lysine side chains of the peptide backbone. The preparation of the conjugate y(KKKe(lipoic acid)EEE)$_3$K is carried out as described in Example 1.5. The peptide/active compound conjugate obtained in this way is investigated for its kidney selectivity after labelling by means of iodine-125 and intravenous administration in the animal model mouse.

Figure 6:
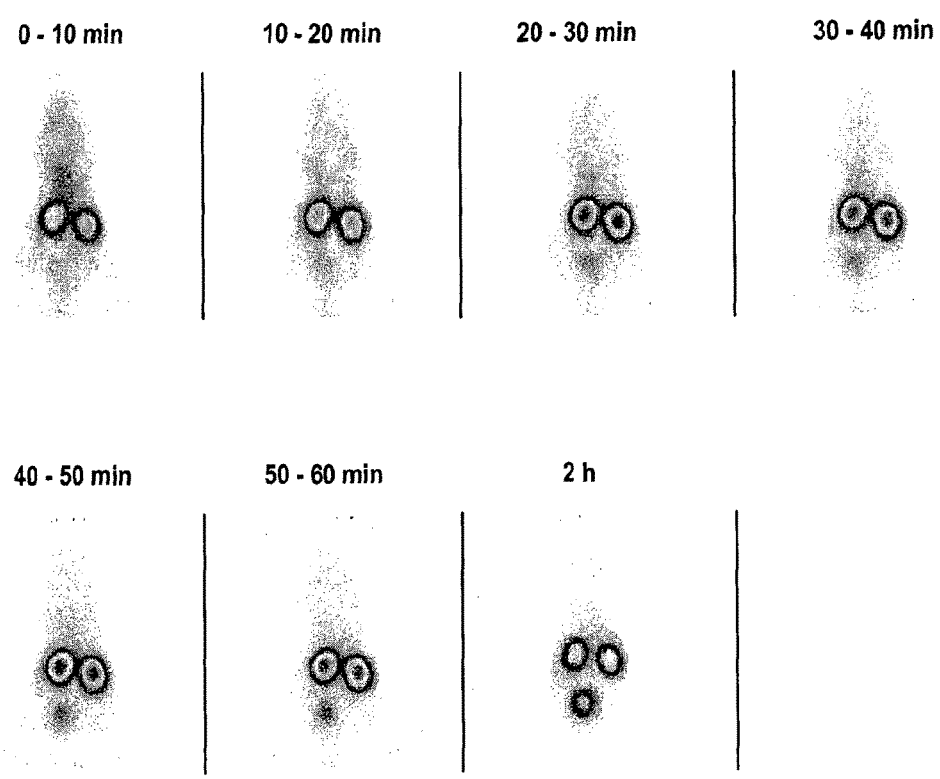
FIG. 6 shows the scintigraphic distribution of $^{125}$I-y (KKKE(lipoic acid)EEE)$_3$K after intravenous administration in an NMRI mouse.

Result (see FIG. 6): the peptide/active compound conjugate prepared has high kidney specificity.

---

The invention claimed is:

1. A conjugate containing at least one kidney-selective carrier molecule and at least one active compound which has a protective action for the kidney against nephrotoxic active compounds,
wherein the at least one kidney-selective carrier molecule is
an oligopeptide comprising multiple monomeric peptides comprising more than 50% (based on the number of amino acid units) of sequence sections selected from the group consisting of -(KKEEE)-, -(RREEE)-, -(KKKEEE)- and -(KKKEE)-, wherein
(i) the peptide or oligopeptide overall has a chain length of 15 to 100 amino acid units;
(ii) the peptide or oligopeptide comprises at least 50% (based on the number of amino acid units) of amino acids K and E, or R and E, respectively; and
(iii) the oligopeptide comprises at least 3 consecutive sequence sections; wherein the at least one active compound is selected from the group consisting of lipoic acid, resveratrol, caffeic acid, luteolin, quercetin, rutin, cyanidin, xanthohumol, ascorbic acid, nicotinic acid, amifostin, alliin, thiols, tocopherols, carotinoids, butylhydroxytoluene (BHT), pifithrin-μ, pifithrin-α, MDL 28170 and NS3694, and combinations thereof.

2. The conjugate of claim 1, wherein the oligopeptide contains 3 to 5 successive sequence sections.

3. The conjugate of claim 1, wherein the oligopeptide is selected from the group consisting of (RREEE)$_3$R (SEQ ID NO: 81), (KKEE)$_5$K (SEQ ID NO: 82), (KKKEE)$_3$K (SEQ ID NO: 83), (KKKEEE)$_3$K (SEQ ID NO: 84) and (KKEEE)$_3$ K (SEQ ID NO: 85).

4. The conjugate of claim 1, wherein the at least one active compound is an antioxidant and/or an apoptosis inhibitor.

5. A pharmaceutical composition comprising at least one conjugate of claim 1 as medicament.

6. A method for the protection of the kidney against nephrotoxic active compounds, comprising administering to a patient in need thereof an effective amount of a pharmaceutical composition of claim 5.

7. The pharmaceutical composition of claim 5, further comprising a pharmaceutically acceptable excipient.

* * * * *